(12) United States Patent
Amit et al.

(10) Patent No.: US 10,458,777 B2
(45) Date of Patent: Oct. 29, 2019

(54) POLARIZATION MEASUREMENTS OF METROLOGY TARGETS AND CORRESPONDING TARGET DESIGNS

(71) Applicant: KLA-TENCOR CORPORATION, Milpitas, CA (US)

(72) Inventors: Eran Amit, Haifa (IL); Barry Loevsky, Yokneam Ilit (IL); Andrew Hill, Sunnyvale, CA (US); Amnon Manassen, Haifa (IL); Nuriel Amir, St. Yokne'am (IL); Vladimir Levinski, Migdal Haemek (IL); Roie Volkovich, Hadera (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/949,444

(22) Filed: Nov. 23, 2015

(65) Prior Publication Data

US 2016/0178351 A1 Jun. 23, 2016

Related U.S. Application Data

(63) Continuation of application No. PCT/US2014/044440, filed on Jun. 26, 2014.
(Continued)

(51) Int. Cl.
*G01B 11/06* (2006.01)
*G01B 11/27* (2006.01)
(Continued)

(52) U.S. Cl.
CPC ............ *G01B 11/06* (2013.01); *G01B 11/272* (2013.01); *G01N 21/9501* (2013.01);
(Continued)

(58) Field of Classification Search
CPC ........................................................ G02F 1/00
(Continued)

(56) References Cited

U.S. PATENT DOCUMENTS 6,023,338 A 2/2000 Bareket
7,528,941 B2 5/2009 Kandel et al.
(Continued)

FOREIGN PATENT DOCUMENTS

CN 1632518 A 6/2005
CN 101416043 A 4/2009
(Continued)

OTHER PUBLICATIONS

Office Action dated Aug. 29, 2018 for Taiwan Application No. 103122413.
(Continued)

*Primary Examiner* — Isiaki O Akanbi
(74) *Attorney, Agent, or Firm* — Suiter Swantz pc llo

(57) ABSTRACT

Targets, target elements and target design method are provided, which comprise designing a target structure to have a high contrast above a specific contrast threshold to its background in polarized light while having a low contrast below the specific contrast threshold to its background in non-polarized light. The targets may have details at device feature scale and be compatible with device design rules yet maintain optical contrast when measured with polarized illumination and thus be used effectively as metrology targets. Design variants and respective measurement optical systems are likewise provided.

20 Claims, 22 Drawing Sheets

Related U.S. Application Data

(60) Provisional application No. 61/840,339, filed on Jun. 27, 2013, provisional application No. 61/916,018, filed on Dec. 13, 2013.

(51) Int. Cl.
   *G01N 21/95* (2006.01)
   *G01N 21/956* (2006.01)
   *G06F 17/50* (2006.01)
   *H01L 21/66* (2006.01)
   *G01N 21/88* (2006.01)

(52) U.S. Cl.
   CPC ....... *G01N 21/956* (2013.01); *G06F 17/5072* (2013.01); *G06F 17/5081* (2013.01); *G01B 2210/56* (2013.01); *G01B 2290/70* (2013.01); *G01N 2021/8848* (2013.01); *H01L 22/30* (2013.01)

(58) Field of Classification Search
   USPC ............... 356/399–401, 237.2–237.6, 243.4, 356/601–614
   See application file for complete search history.

(56) References Cited

U.S. PATENT DOCUMENTS

| | | | |
|---|---|---|---|
| 9,093,458 B2* | 7/2015 | Amir | H01L 23/544 |
| 9,934,353 B2* | 4/2018 | El Kodadi | G01N 21/4785 |
| 2003/0021465 A1* | 1/2003 | Adel | G03F 7/70633 |
| | | | 382/151 |
| 2003/0133102 A1 | 7/2003 | Opsal | |
| 2005/0012928 A1* | 1/2005 | Sezginer | G01B 11/26 |
| | | | 356/401 |
| 2005/0286052 A1* | 12/2005 | Huggins | G03F 9/7076 |
| | | | 356/401 |
| 2006/0028957 A1 | 2/2006 | Kim | |
| 2008/0094630 A1 | 4/2008 | Mieher et al. | |
| 2009/0002706 A1 | 1/2009 | Weiss et al. | |
| 2010/0328636 A1* | 12/2010 | Quaedackers | G03F 7/70625 |
| | | | 355/53 |
| 2010/0330469 A1 | 12/2010 | Marokkey | |
| 2012/0033215 A1* | 2/2012 | Kandel | G03F 7/70683 |
| | | | 356/366 |
| 2012/0123581 A1* | 5/2012 | Smilde | G03F 7/70483 |
| | | | 356/445 |
| 2014/0240705 A1* | 8/2014 | Takimoto | G03F 7/70633 |
| | | | 356/401 |

FOREIGN PATENT DOCUMENTS

| | | |
|---|---|---|
| CN | 101458464 A | 6/2009 |
| JP | 2003247807 A | 9/2003 |
| JP | 2004508711 A | 3/2004 |
| JP | 2006518942 A | 8/2006 |
| JP | 2007096292 A | 4/2007 |
| JP | 2009539109 A | 11/2009 |
| TW | 201220447 A | 5/2012 |

OTHER PUBLICATIONS

Office Action dated Jan. 8, 2019 for JP Patent Application No. 2016-524217.

Brown, Dean P., 2010. Polarization and coherence-engineered illumination with applications in imaging (Doctoral dissertation, University of Rochester).†

Smith, B.W. and Cashmore, J.S., Jul. 2002. Challenges in high NA, polarization, and photoresists. In SPIE's 27th Annual International Symposium on Microlithography (pp. 11-24). International Society for Optics and Photonics.†

* cited by examiner
† cited by third party

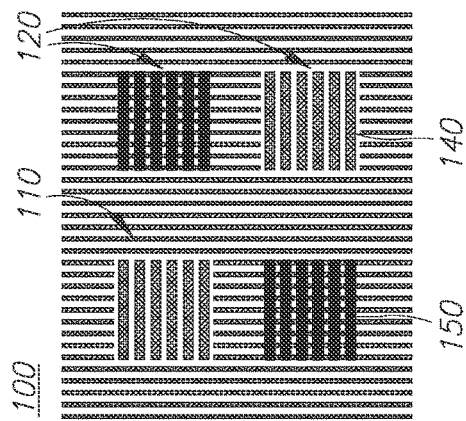
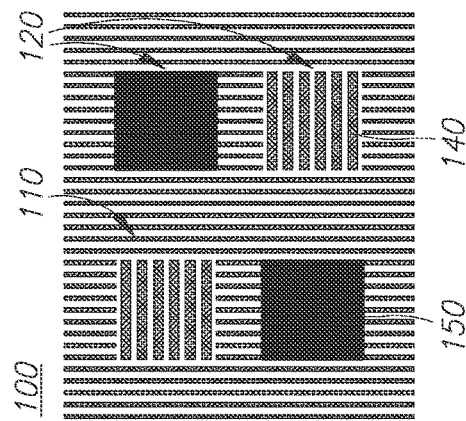
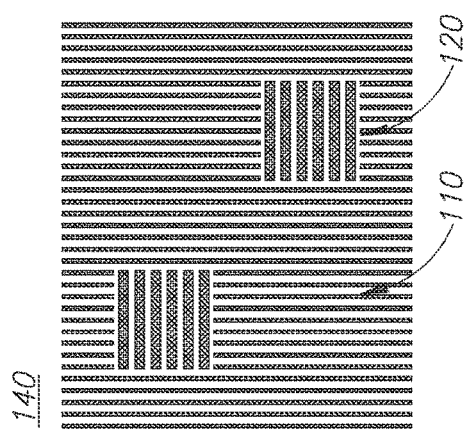
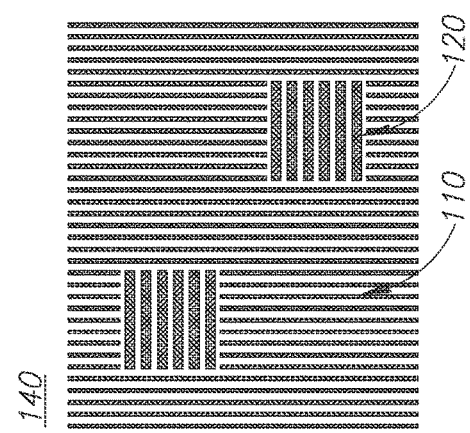
Figure 5A
Figure 5B

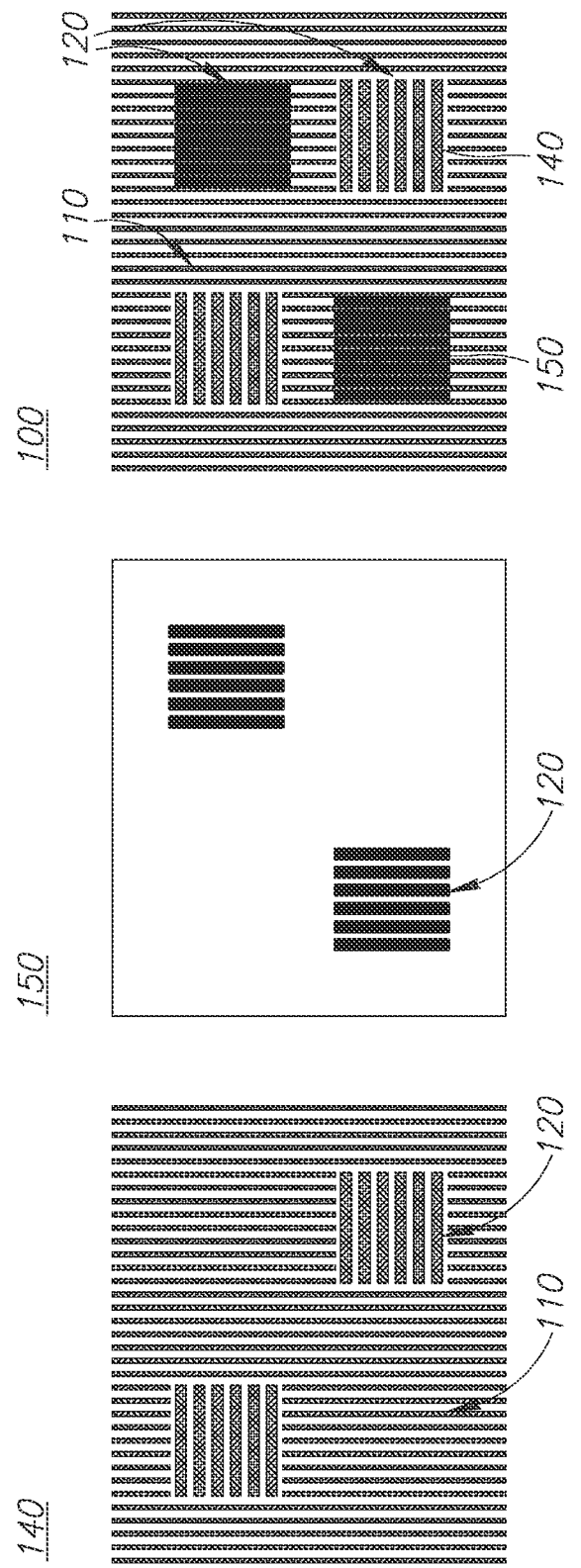

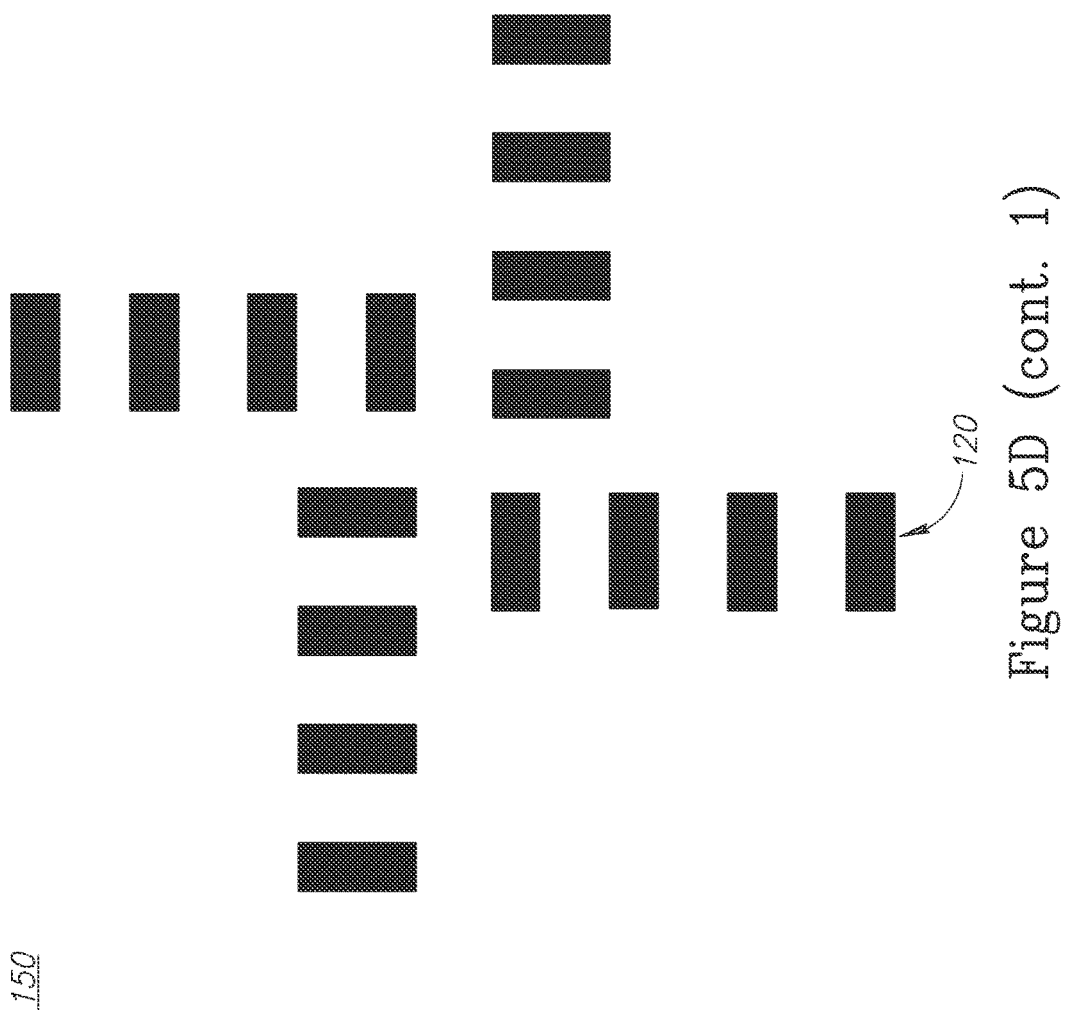

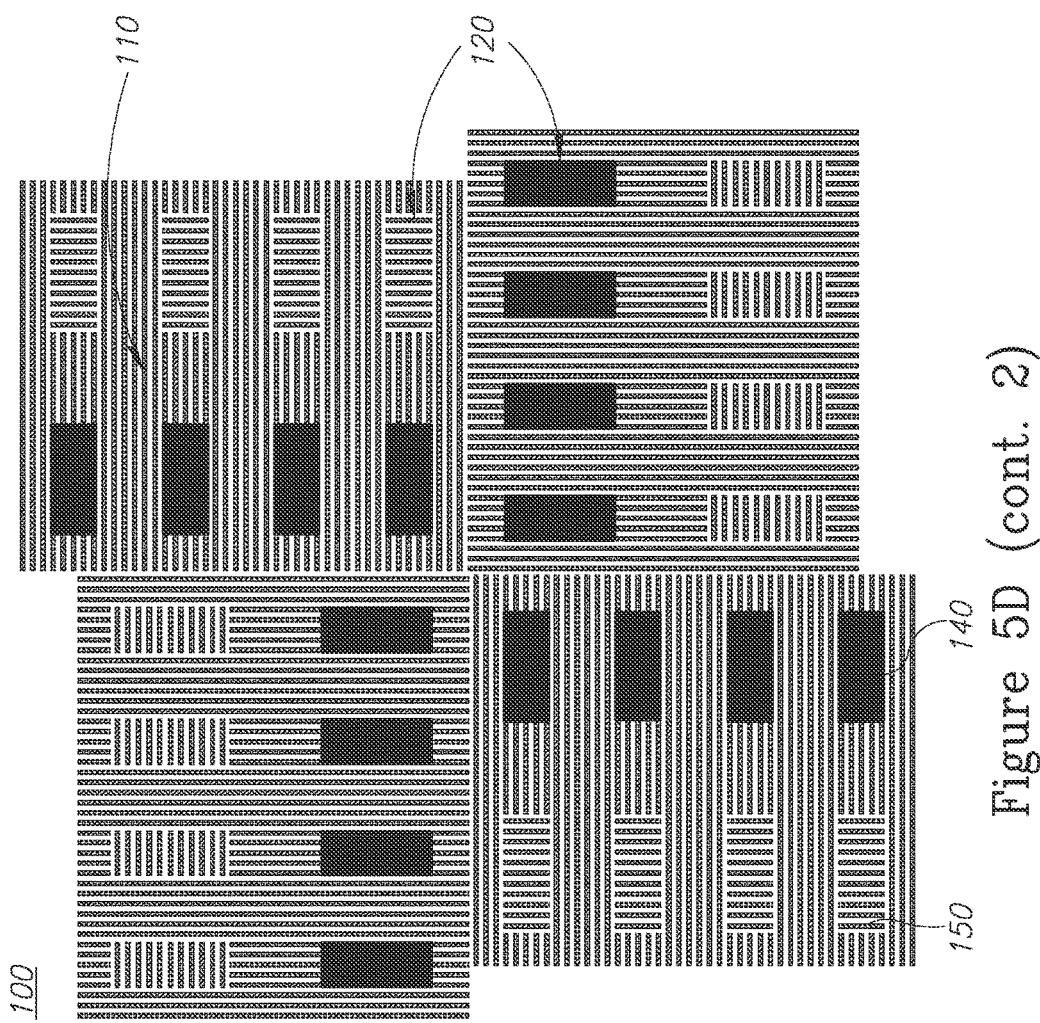

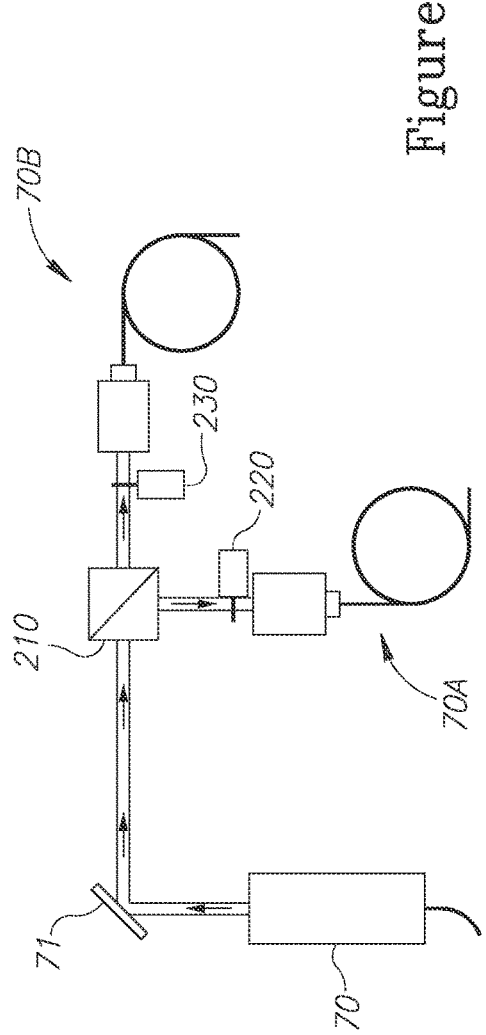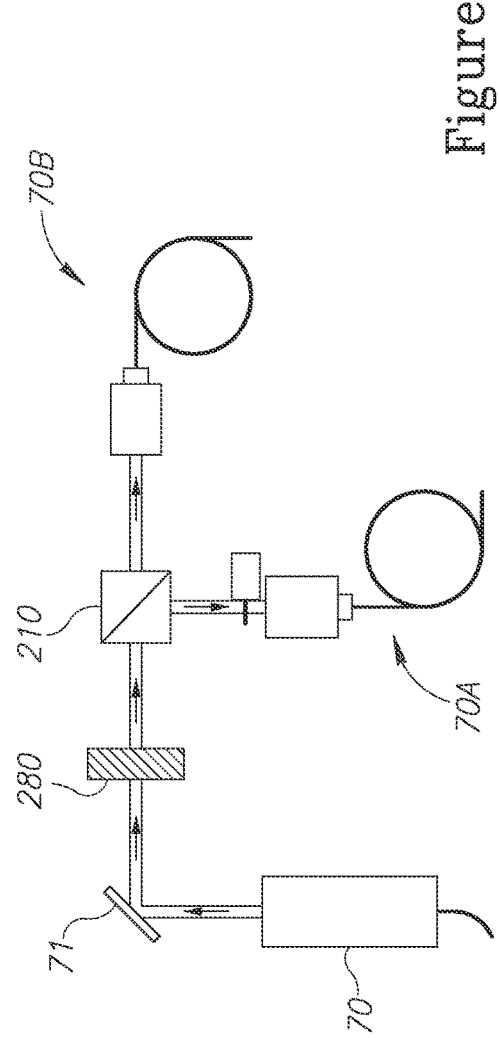

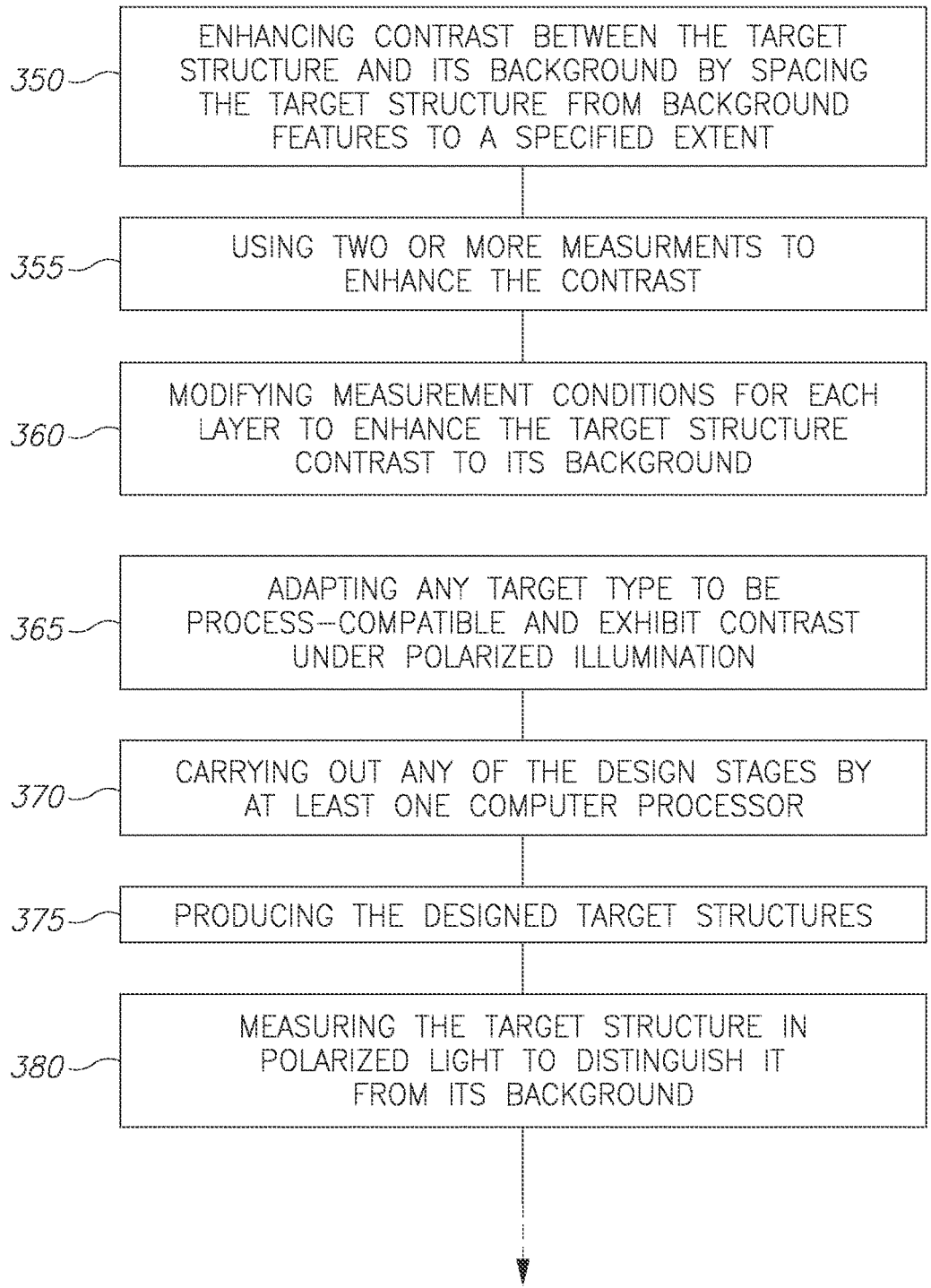
Figure 7 (cont. 1)

390 — CARRYING OUT THE MEASUREMENTS IN POLARIZED LIGHT, USING ANY OF: COUPLED POLARIZERS, ALTERNATING POLARIZERS IN THE OPTICAL PATH, AN INTERFEROMETER, VARIABLE RETARDER POLARIZERS, A ZERO ORDER BLOCKER AT THE PUPIL PLANE AND/OR POLARIZED LIGHT SOURCES

Figure 7 (cont. 2)

POLARIZATION MEASUREMENTS OF METROLOGY TARGETS AND CORRESPONDING TARGET DESIGNS

CROSS-REFERENCE TO RELATED APPLICATIONS

This application is filed under 35 U.S.C. § 120 and § 365(c) as a continuation of International Patent Application Serial No. PCT/US14/44440, filed on Jun. 26, 2014, which application claims the benefit under 35 U.S.C. 119(e) of U.S. Provisional Patent Application No. 61/840,339, filed on Jun. 27, 2013 and U.S. Provisional Patent Application No. 61/916,018, filed on Dec. 13, 2013, which applications are incorporated herein by reference in their entirety.

FIELD OF THE INVENTION

The present invention relates to the field of metrology, and more particularly, to metrology targets.

BACKGROUND OF THE INVENTION

Metrology targets are designed to enable the measurement of parameters that indicate the quality of wafer production steps and quantify the correspondence between design and implementation of structures on the wafer. Metrology targets as specific structures optimize the requirements for device similarity and for optical measurability. Compliance of targets to semiconductor manufacturing design rules contributes to accurate production of the targets but may reduce the optical measurability of the targets.

BRIEF SUMMARY OF THE INVENTION

One aspect of the present invention provides a method comprising designing a target structure to have a high contrast above a specific contrast threshold to its background in polarized light while having a low contrast below the specific contrast threshold to its background in non-polarized light.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout. In the accompanying drawings:

FIG. 5A is a high level schematic illustration of process compatible target designs that maintain contrast by utilizing measurement by polarized light, according to some embodiments of the invention;

FIG. 5B is a high level schematic illustration of process compatible target designs that maintain contrast by utilizing measurement by polarized light, according to some embodiments of the invention;

FIG. 5C is a high level schematic illustration of process compatible target designs that maintain contrast by utilizing measurement by polarized light, according to some embodiments of the invention;

FIG. 6K is a high level schematic illustration of optical illumination and measurement systems, according to some embodiments of the invention;

FIG. 6L is a high level schematic illustration of optical illumination and measurement systems, according to some embodiments of the invention;

DETAILED DESCRIPTION OF THE INVENTION

Figure 1A:
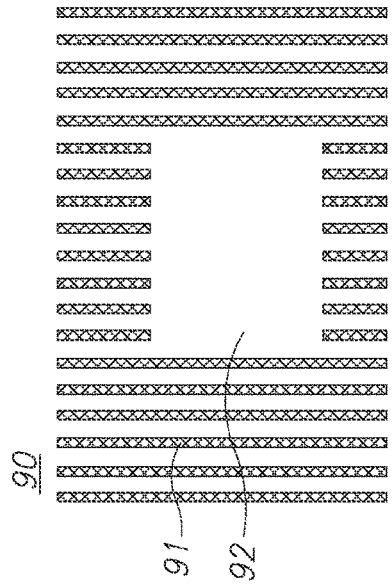
FIG. 1A is a high level schematic illustration of a target element according to the prior art.

Prior to the detailed description being set forth, it may be helpful to set forth definitions of certain terms that will be used hereinafter.

The terms "metrology target" or "target" as used herein in this application, are defined as structures designed or produced on a wafer which is used for metrological purposes. Non-limiting examples for metrology targets are imaging targets such as AIM (Advanced Imaging Metrology), BiB (Box-in-Box), AIMid and BLOSSOM and their corresponding variations and alternatives; and scatterometry targets such as SCOL (Scatterometry Overlay) and their corresponding variations and alternatives. The term "target element" is used herein in this application to refer to a part of a full target, which is designed according to the disclosed principles. Thus, any target element may be immediately used to design a full target; hence targets are referred to in the current application in terms of their target element designs and interchangeably therewith.

The term "target structure" as used herein in this application, is defined as a feature in the metrology target such as individual target areas or boxes, grating bars etc. Target structures may be full or empty (gaps), and may also be segmented, i.e., may comprise multiple smaller features which cumulatively constitute the target structure. A target and/or a periodic structure is referred to as comprising target structure, each "target structure" being a feature of the target that is to be distinguished from its background, the "background" being a wafer area proximate to a target structure on the same or on a different layer (above or below the target structure). The term "layer" as used herein in this application, is defined as any of the layers used in a photolithography process in any of its steps. The terms "continuous structure", "empty region" or "full bar" as used herein in this application, are defined as continuous target structures such as empty regions or full bars having dimensions which are large with respect to typical device features. While most of the description refers to empty background regions rather than to full ones, it is explicitly noted that similar design principles are applicable to full backgrounds and respectively designed targets are likewise part of the disclosed invention.

The terms "metrology measurement" or "measurement" as used herein in this application, are defined as any metrology measurement procedure used to extract information from metrology targets. For example, metrology measurements may be imaging of the targets or scatterometry measurements of the targets. Non-limiting examples for metrology measurements include overlay measurement (imaging or scatterometry), critical dimension (CD) measurement, focus and dose measurement etc. The term "overlay" as used herein in this application, is defined as a shift between layers which includes an unintentional component due to process inaccuracies) that may cause production inaccuracies and is thus aim of a metrology measurement. The term "measurement direction" as used in this application refers to the direction along which a target structure is measured, for example, a direction along which the periodic structure is periodic. For example, the measurement direction of a grid as the periodic structure is perpendicular to the target elements (e.g., bars or segmented bars) which constitute the grid.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Targets, target elements and target design methods are provided, which comprise designing a target structure to have a high contrast above a specific contrast threshold to its background in polarized light while having a low contrast below the specific contrast threshold to its background in non-polarized light. The targets may have details at device feature scale and be compatible with device design rules, yet maintain optical contrast when measured with polarized illumination and thus be used effectively as metrology targets. Design variants and respective measurement optical systems are likewise provided. While current optical overlay targets contain features which are much bigger than the device and as a result suffer from more process damages, the disclosed targets provide contrast from polarization properties, are more process compatible and therefore represent the device overlay more accurately. Additional techniques to improve the contrast are also described below.

Figure 1B:
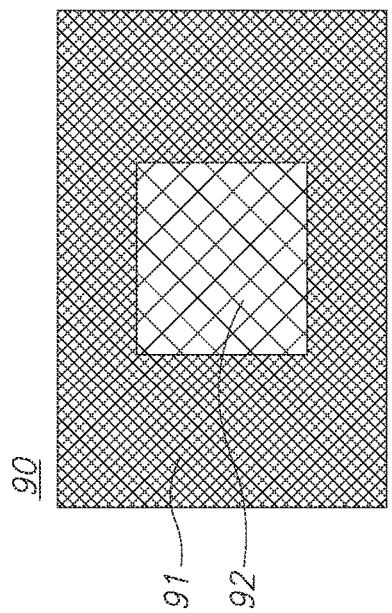
FIG. 1B is a high level schematic illustration of a target element according to the prior art.

FIGS. 1A and 1B are high level schematic illustrations of target elements 90 according to the prior art. Currently used target structures 92 are continuous, either fill (FIG. 1A) or empty (FIG. 1B) and exhibit optical contrast in coherent (or incoherent) illumination with respect to their backgrounds 91, to enable imaging metrology (e.g., overlay measurements). For example, FIG. 1A schematically illustrates target structure 92 in a current layer over background 91 in a previous layer, with both target element 92 and background 91 being continuous. Target structures 92 may be areas made mostly of one material while backgrounds 91 may be areas made mostly of a different material. In another example, FIG. 1B schematically illustrates target structure 92 as a gap in the same layer as background 91, which is segmented. Background segmentation (termed "dummification") is applied to make target elements 90 more process compatible, and the segmentation is usually carried out in an unresolved manner, i.e., using a small pitch (e.g., in the order of magnitude of 50 nm). As the typical dimension for currently used continuous target structures 92 is 1 µm, production processes such as etch and polish tend to introduce process-related production inaccuracies which are very sensitive to the process. Additionally, imaging targets may not represent the device correctly (e.g., the measured overlay may differ from the actual overlay) and even scatterometry targets may have target structures which are too big with respect to actual device features (e.g., several hundred nm vs. tens of nm, respectively). In imaging, the required contrast arises from the difference in the "filling factor" of different areas, which is the difference in reflection between target structures 92 and their backgrounds 91. Thus, if target structures 92 are segmented to overcome the process-related inaccuracies, their contrast to their backgrounds 91 fades and they are not useful as targets.

Figure 2:
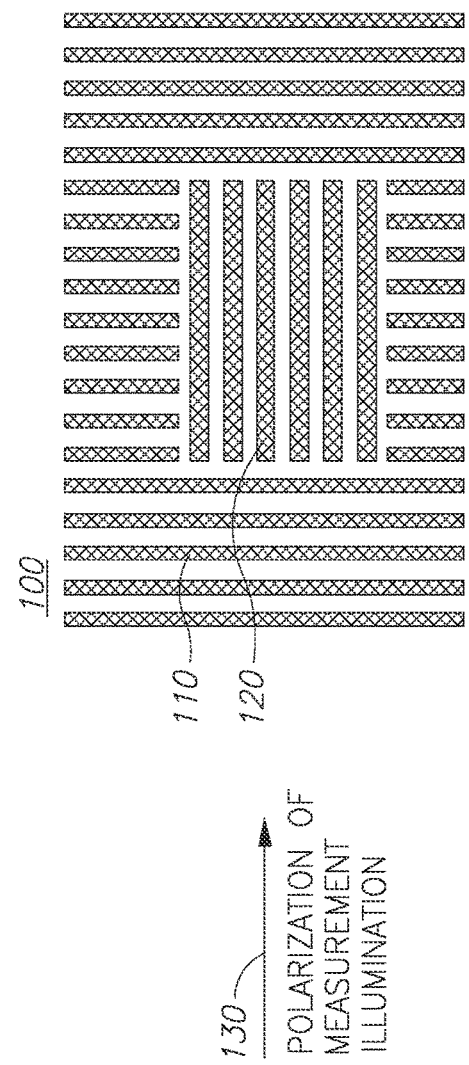
FIG. 2 is a high level schematic illustration of a target structure and its background, being part of a metrology target element, according to some embodiments of the invention.

FIG. 2 is a high level schematic illustration of a target structure 120 and its background 110, being part of a metrology target element 100, according to some embodiments of the invention. In contrast to prior art target elements 90, disclosed metrology target elements 100 comprise segmented target structures 120 as well as segmented backgrounds 110, and use polarized illumination to distinguish therebetween, thereby overcoming the problem of fading contrast upon introduction of segmentation. Advantageously, the disclosed invention uses the difference in the polarization activities of different areas rather than the difference in reflection properties. The disclosed design principles may be applied to any periodic or non-periodic target element 100 in any design metrology target.

Disclosed metrology targets comprise at least target structure 120 arranged to have a high contrast above a specific contrast threshold to its background 110 in polarized light while having a low contrast below the specific contrast threshold to its background 110 in non-polarized light. The specific contrast threshold is given by the used optical equipment or may be configured by adjusting the optical equipment to target specifications. For example, in the example illustrated in FIG. 2, target element 100 may be illuminated with linearly polarized light having a polarization 130 that is parallel to the segmentation lines of target structure 120. The reflection difference between target structure 120 and background 110 arises from the interaction of the polarized illumination with the segmentation features and the influence of their respective directions on the measured signal. For example, segmentation pitch, critical dimension of segments, segmentation direction and segmentation pattern may vary between target structure 120 and background 110.

In certain embodiments, target structure 120 comprises features which are perpendicular to background features of target element 100. Other angles may be set between segmentation features of target structure 120 and background 110. For example, segmentation of any of the elements and/or backgrounds may be diagonal. In certain embodiments, different polarization-altering patterns may be applied to target structure 120 and to background 110. Illumination polarization must not be linear but may also be of any other specified characteristics circular, modulated etc.) and segmentation features may respectively be adapted to yield a difference in changing the illumination polarization in a way that enables distinguishing target structure 120 from background 110.

In certain embodiments, the disclosed invention allows segmenting both target structure 120 and background 110 at a fine pitch, which may be selected to resemble device features. Such targets 100 represent device features better than existing targets, thus providing more accurate measurements, and are still well measurable using polarized illumination, thus not compromising accuracy and contrast as prior art targets do.

In certain embodiments, the ends of the segmentation lines at the border regions between target structures 120 and their respective background 110 are produced to control and enhance contrast between target structures 120 and backgrounds 110 in polarized illumination. In certain embodiments, target structure 120 may be spaced from background features thereof to a specified extent (see e.g., FIG. 4B below).

In certain embodiments, targets 100 are disclosed which further comprise additional layers in a region of target structure 100, to maintain or to enhance the contrast of target structure 120 to its background 110 in polarized light.

Figure 3A:
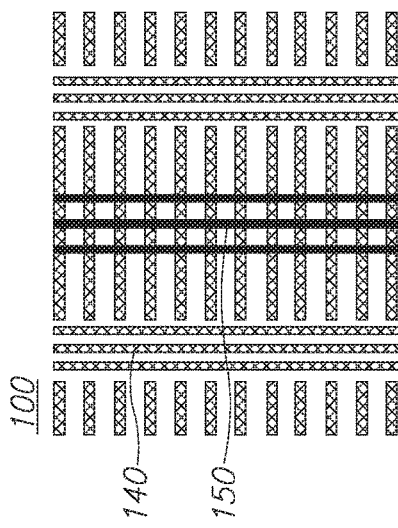
FIG. 3A is a high level schematic illustration of a target designed to have contrast in polarized illumination, according to some embodiments of the invention.
Figure 3B:
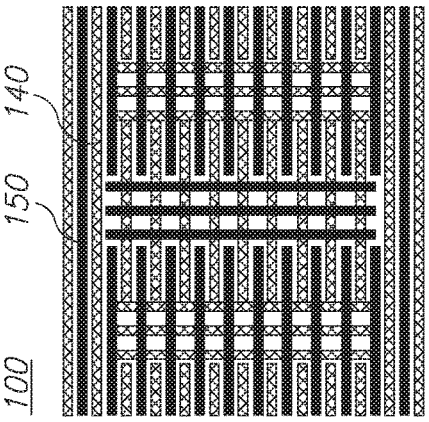
FIG. 3B is a high level schematic illustration of a target designed to have contrast in polarized illumination, according to some embodiments of the invention.
Figure 3C:
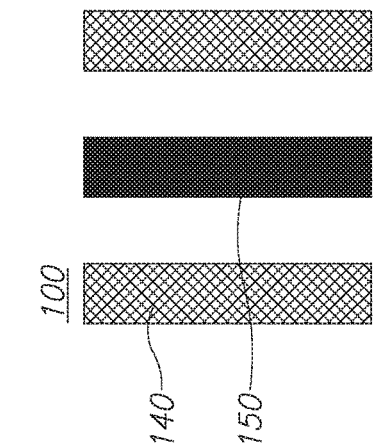
FIG. 3C is a high level schematic illustration of a target designed to have contrast in polarized illumination, according to some embodiments of the invention.

FIGS. 3A-3C are high level schematic illustrations of targets 100 designed to have contrast in polarized illumination, according to some embodiments of the invention. Starting from target structures such as bars in layers 140, 150 (previous and current layer, respectively, see FIG. 3A), targets structures 120 and their backgrounds 110 are segmented, e.g., perpendicularly, to yield contrast when illuminated in polarized illumination. FIG. 3B schematically illustrates an example in which targets structures 120 and their backgrounds 110 are segmented in previous layer 140 while backgrounds 110 in current layer 150 are left unsegmented (with target structure 120 in current layer segmented). FIG. 3C schematically illustrates an example in which targets structures 120 and their backgrounds 110 are segmented at both previous layer 140 and current layer 150. In FIG. 3C, previous layer 140 and current layer 150 are shown separately in addition to target element 100 in which layers 140, 150 are superposed. Segments 142 of targets structures 120 at previous layer 140 and segments 152 of targets structures 120 at current layer 150 may have the same or differing dimensions and characteristics (like pitch, end configuration etc.). Segments 141 of background 110 at previous layer 140 and segments 151 of background 110 at current layer 150 may have the same or differing dimensions and characteristics (like pitch, end configuration etc.). Furthermore, segmentation in different measurement directions (e.g., x and y) may have different characteristics.

In certain embodiments, first (or higher) order diffraction patterns of targets 100 may be measured to enhance the contrast between targets structures 120 and their backgrounds 110. Measuring first order SCOL (at the pupil plane) or first order images (at the field plane) may enhance the information which is derived from the polarized illumination. Zeroth order diffraction pattern may be blocked or removed by interference to further enhance contrast.

Figure 4A:
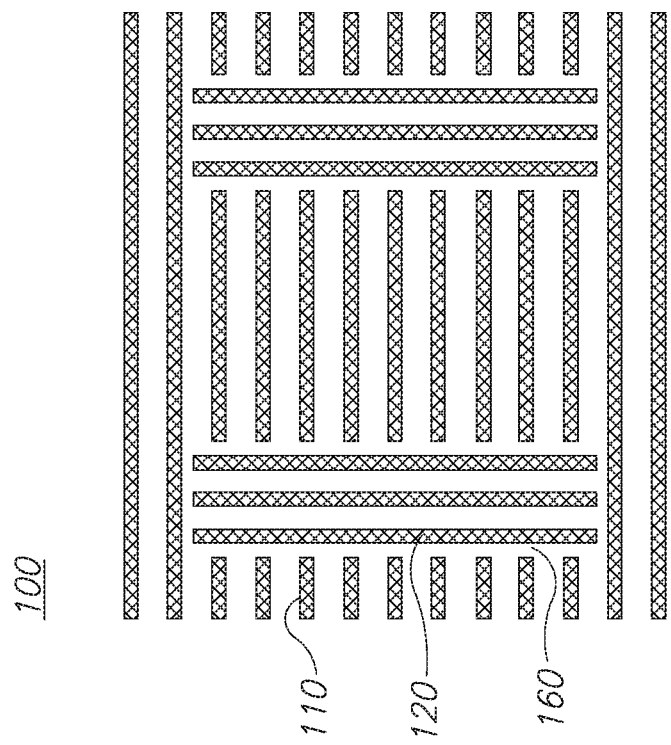
FIG. 4A is a high level schematic illustration of segmentation modifications in a target, according to some embodiments of the invention.
Figure 4B:
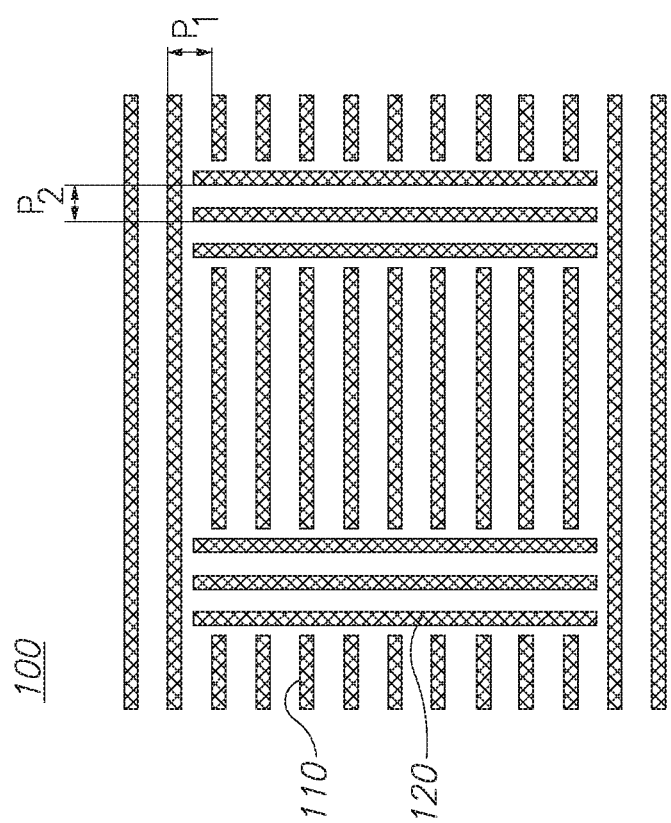
FIG. 4B is a high level schematic illustration of segmentation modifications in a target, according to some embodiments of the invention.

FIGS. 4A and 4B are high level schematic illustrations of segmentation modifications in targets 100, according to some embodiments of the invention. FIG. 4B schematically illustrates spacing segmentation of target structures 120 from segmentation of background 110, with respect to FIG. 4A in which the segments interconnect. Introducing spaces 160 may improve the contrast therebetween under illumination with polarized light. Exact configuration of spaces 160 and line ends may be carried out to further enhance the contrast, using simulation or experimental settings. Segmentation pitches p1, p2 of target structures 120 and background 110 may be equal or differ, and segmentation pitches in X and Y directions may be equal or differ.

In certain embodiments, spaces 160 may be arranged to be measurable with or without use of polarized illumination. For example, spaces 160 may be in the order of magnitude of 100 nm wide. Spaces 160 may be configured to further enhance the contrast for polarized illumination measurements.

In certain embodiments, using polarized light measurements enables segmenting target structures 120 and/or background 110 and makes them thus more process compatible, while using polarized light instead of non-polarized illumination for measurements maintains or even enhances the contrast between target structures 120 and background 110 with respect to unsegmented target structures 120 and/or background 110.

Figure 4C:
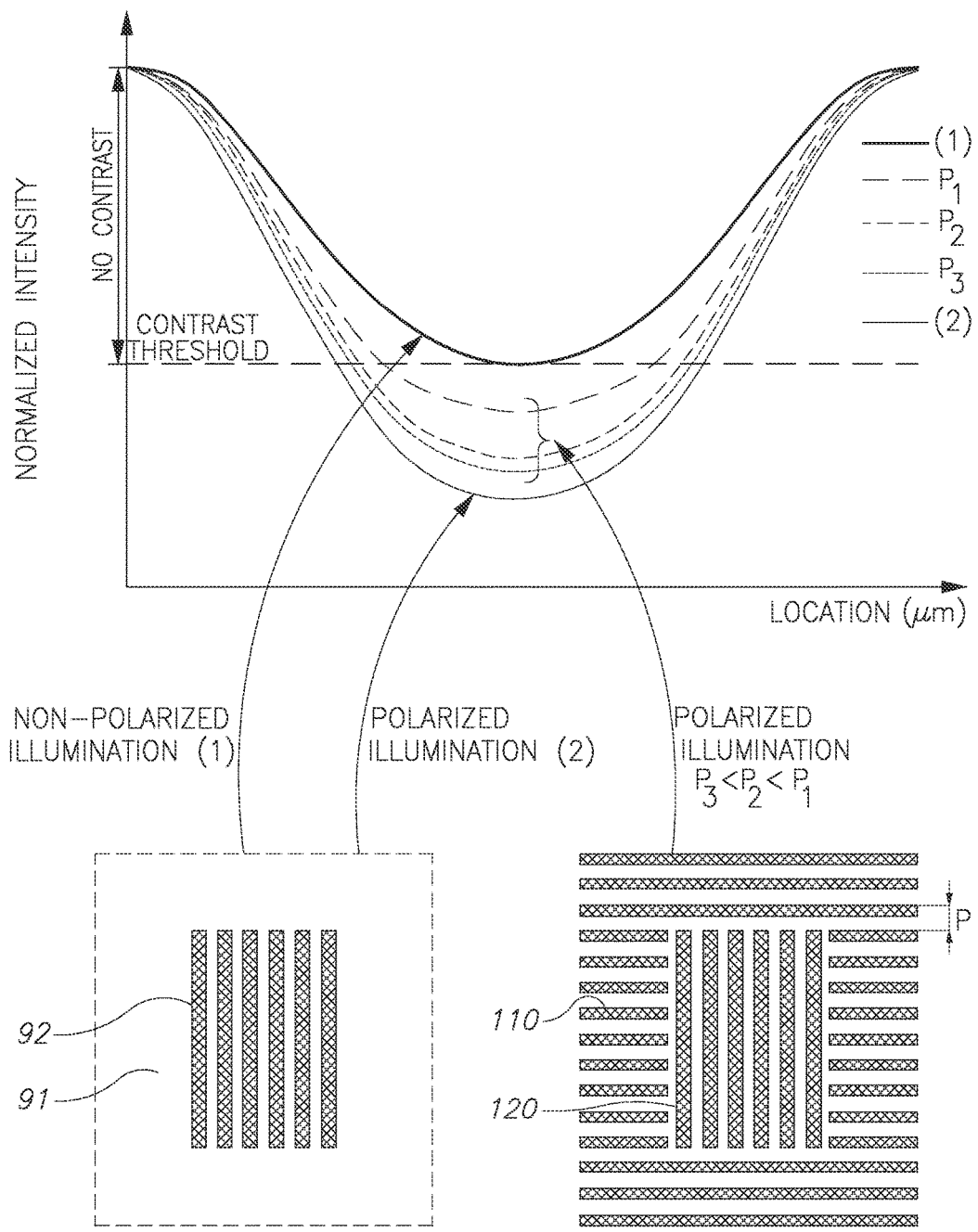
FIG. 4C is a schematic illustration of simulation results of measurements of segmented target structure on continuous and on segmented background in polarized and non-polarized light, illustrating a much better contrast of the former, according to some embodiments of the invention.

For example, FIG. 4C is a schematic illustration of simulation results (for AIM-like targets) of measurements of segmented target structure 92 on continuous background 91 (comparable to FIG. 1B above) in polarized and non-polarized light, illustrating a much better contrast of the former, FIG. 4C further illustrates measurements with polarized illumination of segmented target structure 120 on segmented background 110 (comparable to FIG. 2), which under non-polarized illumination produce no contrast at all. While polarized light measurements yield less contrast for target structure 120 than for target structure 92, they still yield higher contrast than measurements of target structure 92 on non-segmented background 91, and have the significant advantage of being more process compatible than the latter. Moreover, adjustment of segmentation pitch enables adjustment of contrast with respect to measurement conditions, as illustrated by the varying contrast with respect to three background pitches p, p3<p2<p1 (in the illustrated case, the smaller the pitch the higher the contrast under polarized illumination). Furthermore, in case the contrast threshold is at or below the values achieved by non-polarized illumination, any of the polarized light measurements is below the threshold, thus providing sufficient contrast for measurements.

In certain embodiments, metrology measurements of targets 100 may be carried out by multiple acquisition techniques and under different measurement conditions, for example, using any of: different polarization directions (e.g., reducing results for orthogonal polarization with respect to direction 130), spectral variation (color), focus variation, different numerical aperture (NA) size, etc. Several measurements with polarized illumination may be combined to enhance the contrast of target structures in composite images. For example, altering the focus between the measurements, or changing the wavelength between the measurements may provide further information that enhances contrast under polarized light measurements.

FIGS. 5A-5F are high level schematic illustrations of process compatible target designs 10 that maintain contrast by utilizing measurement by polarized light, according to some embodiments of the invention. Difference in the polarization activities of different areas in targets 100 may be used to derive metrology measurements instead or in addition to differences in reflection properties. For example, linear polarized light may be used to distinguish areas having horizontal lines from areas having vertical lines, depending on the polarization activity of the materials and the segmentation pitch. Using polarized light may thus enable designing targets with features and intermediate spaces which have dimensions in the order or magnitude of the device features and spaces to improve the correspondence of measured target overlays and device overlays.

FIGS. 5A-5E schematically illustrate common target designs, modified according to the present invention, by illustrating previous layer 140, current layer 150 and resulting compound targets 100. Target structures in either layer are denoted by the numeral 120, while segmented backgrounds are denoted by the numeral 110 as above. The examples are non-limiting with respect to segmentation details, which may be modified and adapted according to specific requirements, nor are they limiting with respect to exact target designs, but serve to illustrate the implementation of the disclosed design principles to common target designs.

FIGS. 5A-5C schematically illustrate alternative designs for AIMID-like targets that enable two dimensional overlay measurements. Similar principles may be applied to other target designs such as BiB and Blossom targets. While, in a non-limiting manner, all three designs have the same background segmentation 110 and target segmentation 120 at previous layer 140, they differ in the segmentation of targets 120 in current layer 150, which may be missing (FIG. 5B), parallel (FIG. 5A) or perpendicular (FIG. 5C) to the segmentation of targets 120 in previous layer 140. Clearly, any segmentation feature of any of the elements may be modified according to requirements and pitch in either direction and in either structure may be varied. Appropriate measurement conditions (e.g., polarization details, wavelengths) may be applied to yield contrast between target structures 120 and their background 110. In certain embodiments, an overlay may be induced between elements of layers 140, 150 (see e.g., target structures 120 in target 100 in FIG. 5C) to enable scatterometry measurements of target 100 as well as imaging measurements thereof.

Figure 5D:
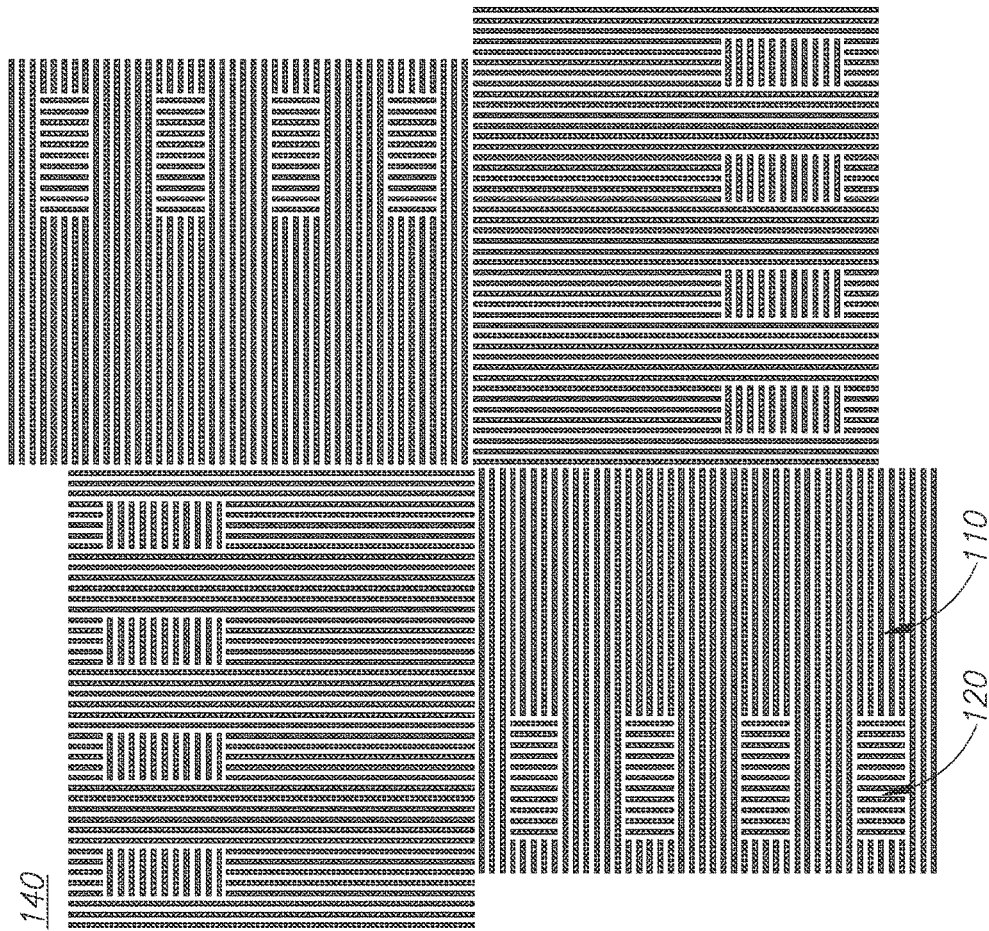
FIG. 5D is a high level schematic illustration of process compatible target designs that maintain contrast by utilizing measurement by polarized light, according to some embodiments of the invention.
Figure 5E:
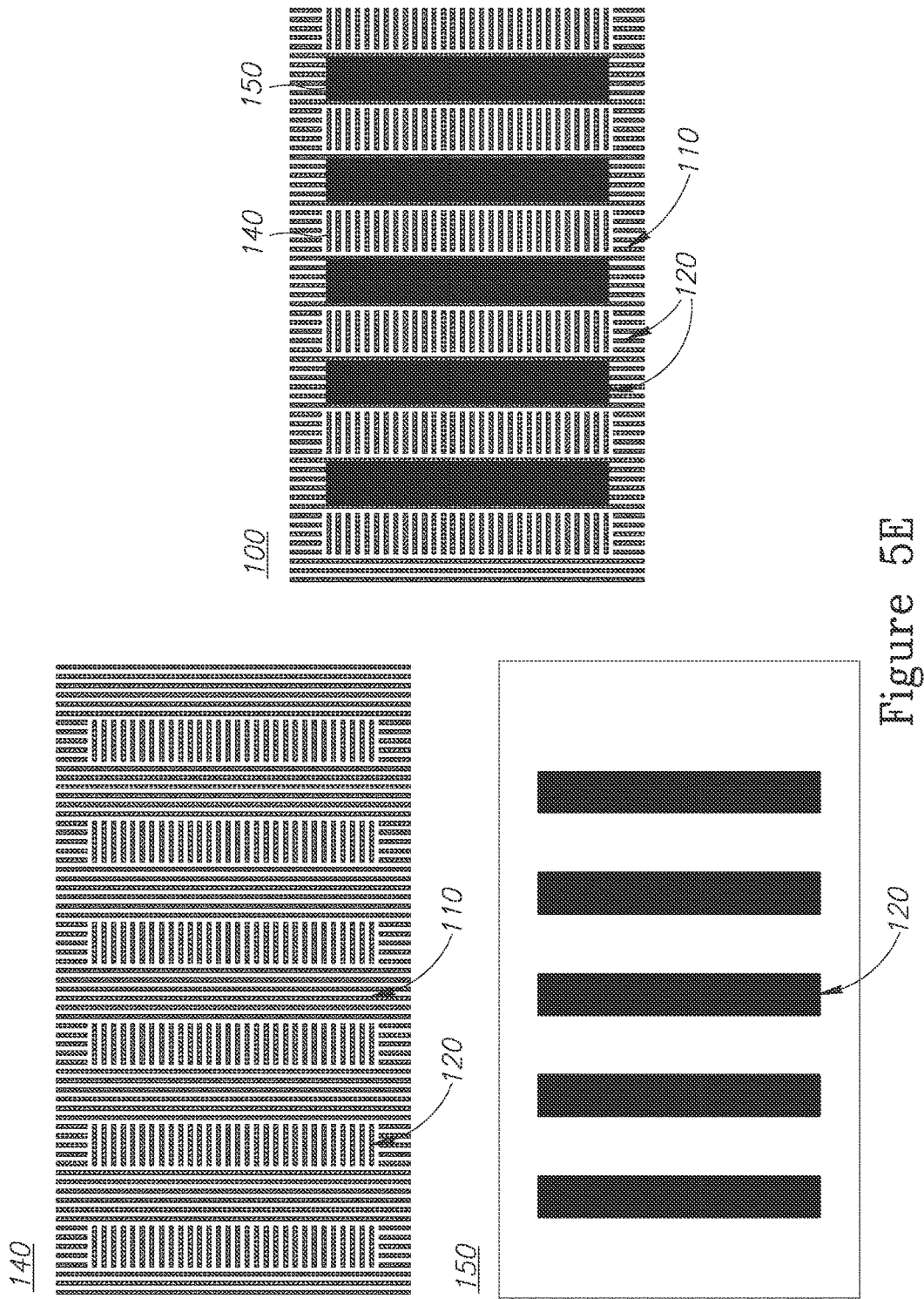
FIG. 5E is a high level schematic illustration of process compatible target designs that maintain contrast by utilizing measurement by polarized light, according to some embodiments of the invention.
Figure 5F:
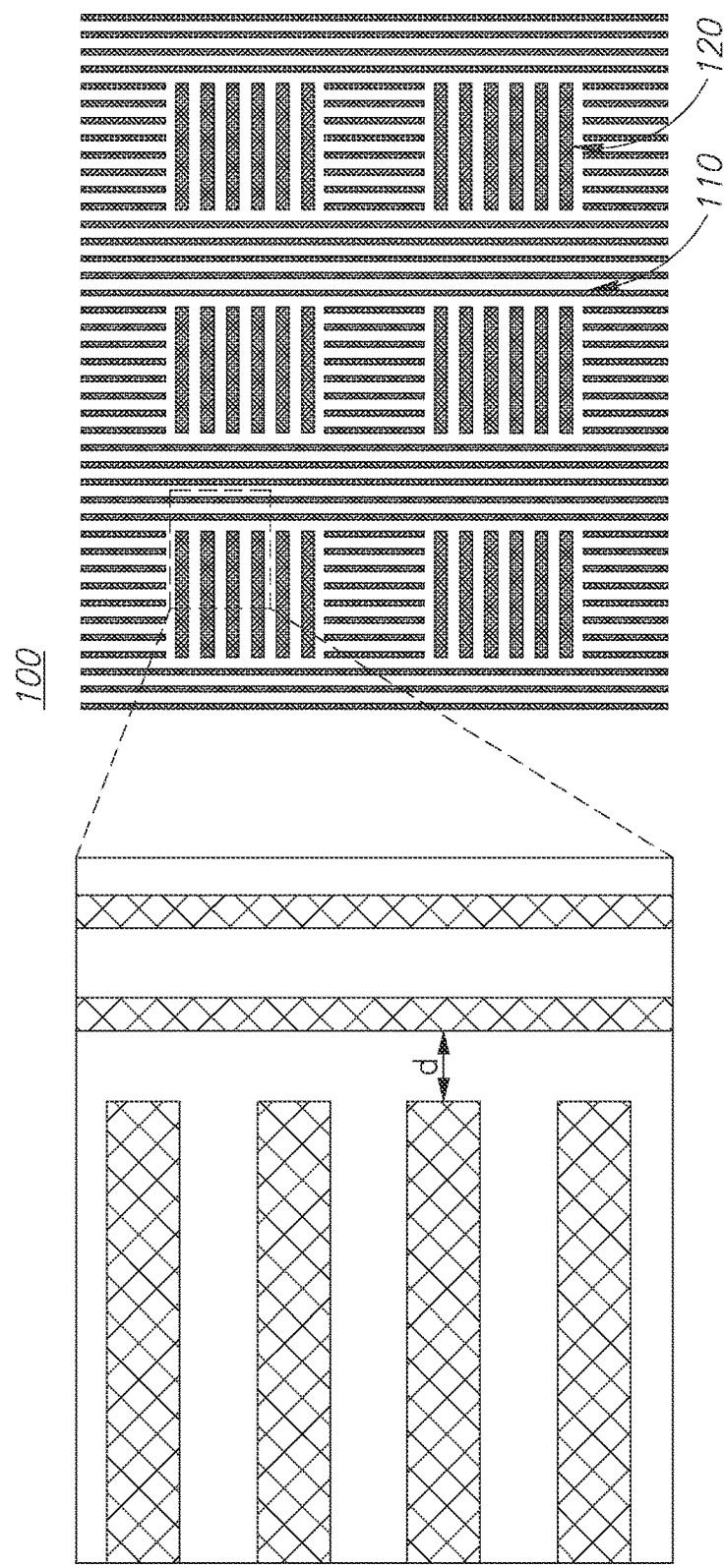
FIG. 5F is a high level schematic illustration of process compatible target designs that maintain contrast by utilizing measurement by polarized light, according to some embodiments of the invention.

FIG. 5D schematically illustrates a segmented design for AIM-like targets that enable two one-dimensional overlay measurements. FIG. 5E schematically illustrates a segmented design for scatterometry targets that enable scatterometry measurements. FIG. 5F schematically illustrates a segmented design with enlarged features, which may be applicable to any of the above designs. FIGS. 5D and 5E represent merely single examples for the application of the disclosed design principles to such respective targets, and the whole variety of possible designs according to the guidelines disclosed above is considered to be disclosed herein. In the illustrated cases, background 110 and target structures 120 in previous layer 140 are segmented perpendicularly, while target structures in current layer 150 are continuous (i.e., or gap bars). Segmentation may be applied to either or both background and targets structures in current layer 150, in different orientations with respect to the segmentation of background 110 and target structures 120 in previous layer 140. Relative segmentation orientation background 110 and target structures 120 in previous layer 140 may also be modified, and measurement conditions (e.g., polarization details, wavelengths) may be adjusted accordingly.

Referring to FIG. 5F, the distances d between segmentation features of background 110 and target structures 120 may be selected to optimize the measurements associated with target structures 120 using polarized light having specified characteristics (wavelengths, type and direction of polarization etc).

The reflection of the boundary between target structures 120 and background 110 having different orientations may be strongly dependent on the quality and characteristics of the line ends, line edge roughness and the distance between the lines. Targets 100 similar to those illustrated in FIG. 5F may be used to quantify and monitor these parameters. For example, the side wall angle (SWA) may be indicative of distances d, e.g., identical SWAs may indicate identical distances d for all lines white differences in line SWA may be used as indication for pattern placement error or big variations in the line ends and edges quality. In certain embodiments, distances d may be varied among parallel lines (by design), within a small range of a few nanometers. Under such small changes, the side wall angle should be proportional to the change in distance d, and any deviation from such proportional behavior may be used to indicate the quality of the lithography process, and, as the patterning is at the device's scale, the dependency SWA(d) may be used as a direct indication for the device quality. In certain embodiments, intentional variation of distances d may be used in optical CD targets to enhance target sensitivity to scanner focus and dose variations for monitoring and control purposes. In certain embodiments, polarization parameters may be changed to extract additional information from the targets different responses to different polarization parameters.

FIGS. 6A-6M are high level schematic illustrations of optical illumination and measurement systems 200, according to some embodiments of the invention. In all figures, a non-polarized light source 70 is modified to provide polarized illumination of target 100 on wafer 75 via objective 77. The collected illumination directed via lens 79 to detector 80 (such as a CCD camera)—may be polarized similarly to or differently from the illumination.

Figure 6A:
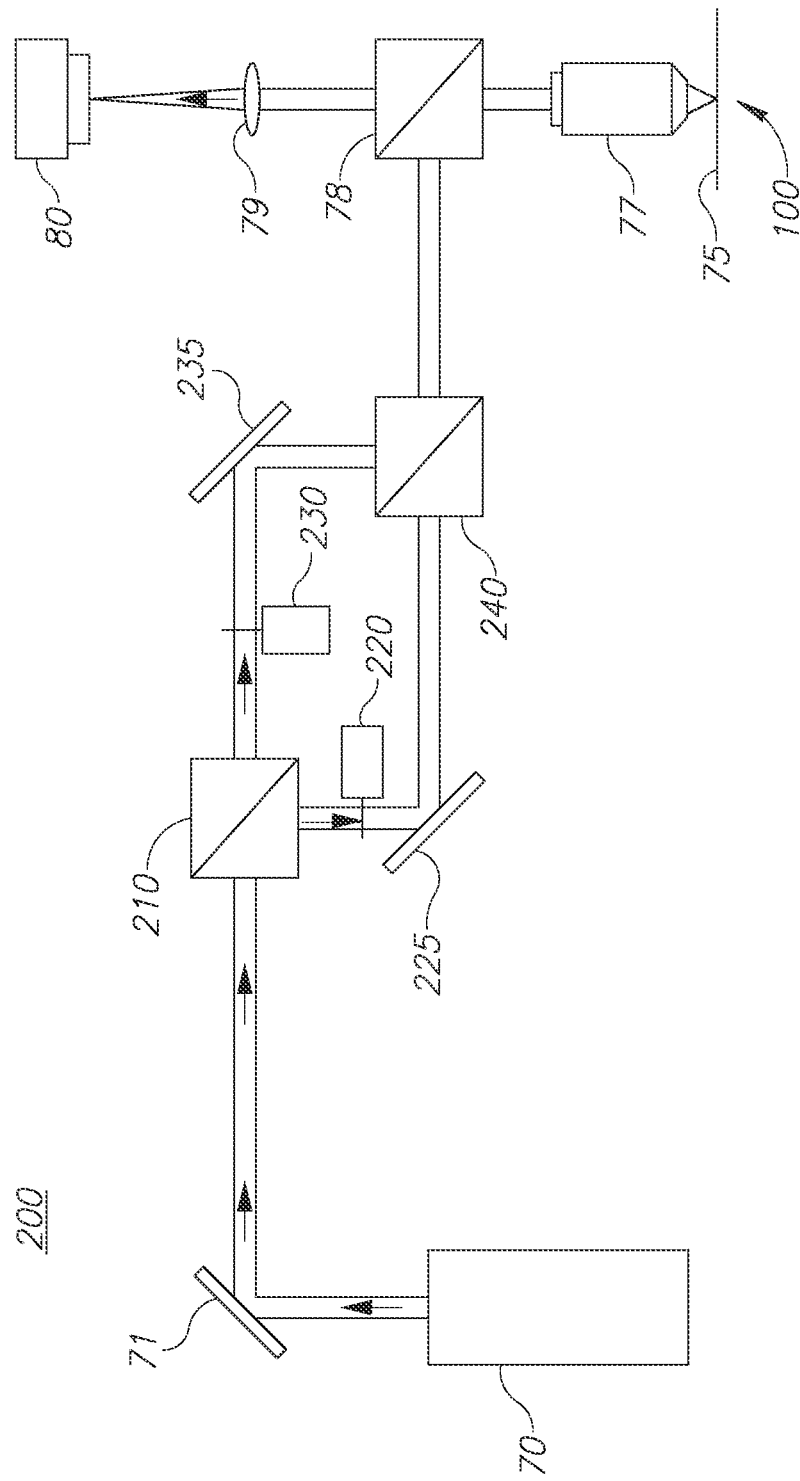
FIG. 6A is a high level schematic illustration of optical illumination and measurement systems, according to some embodiments of the invention.
Figure 6B:
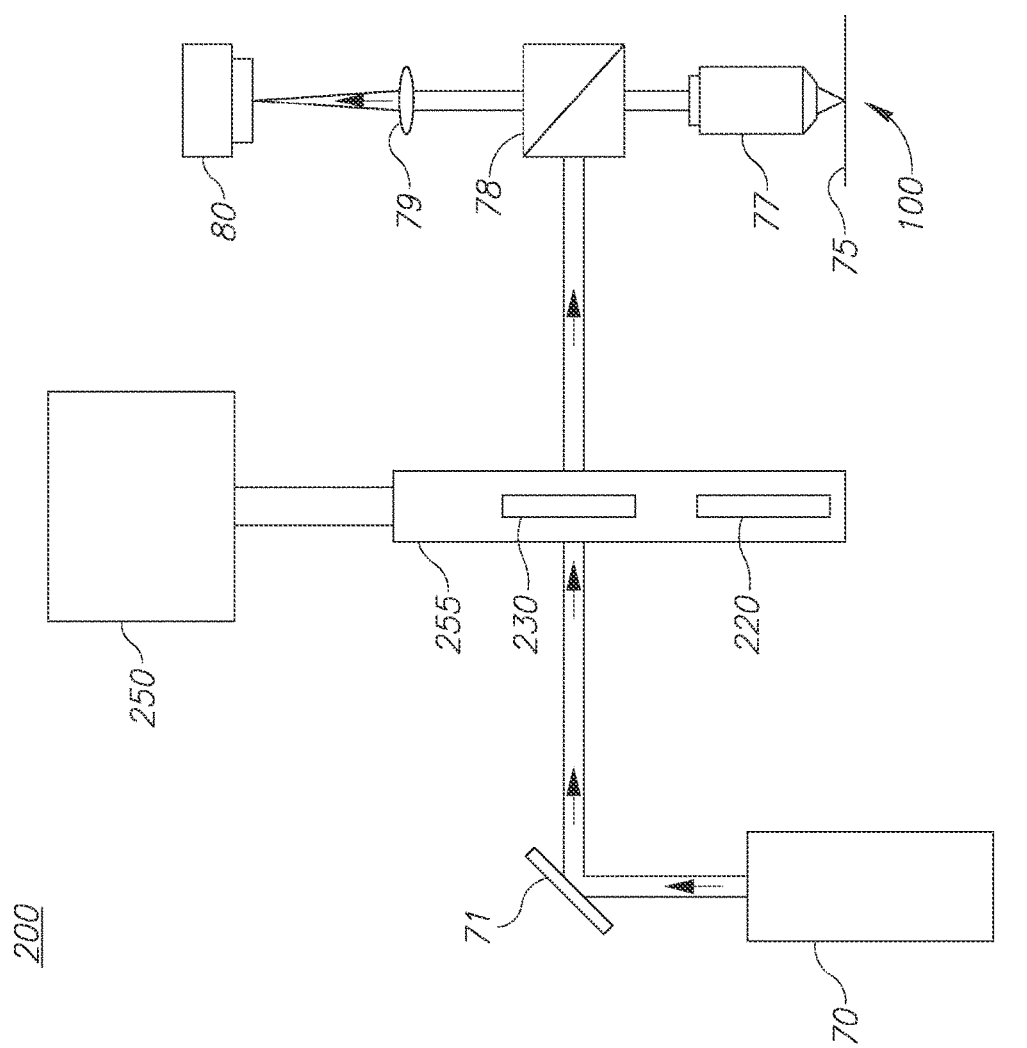
FIG. 6B is a high level schematic illustration of optical illumination and measurement systems, according to some embodiments of the invention.

For example, FIG. 6A schematically illustrates using a Polarizing Beam Splitter (PBS) 210 with shutters 220, 230 and mirrors 225, 235 respectively for handling two types of polarization (e.g., s- and p-polarization) in the respective arms. The resulting illumination beam is combined from the two arms through beam splitter 240 and conducted to the optical axis of the measurement via beam splitter 78. In this configuration, the polarization of the illumination beam is controlled by shutters 220, 230. In another example, FIG. 6B illustrates implementing illumination polarization by controlling polarizers 220, 230 which may be embedded in a rotating or translating plate 255 associated with an actuator 250 used to modify illumination beam polarization.

Figure 6D:
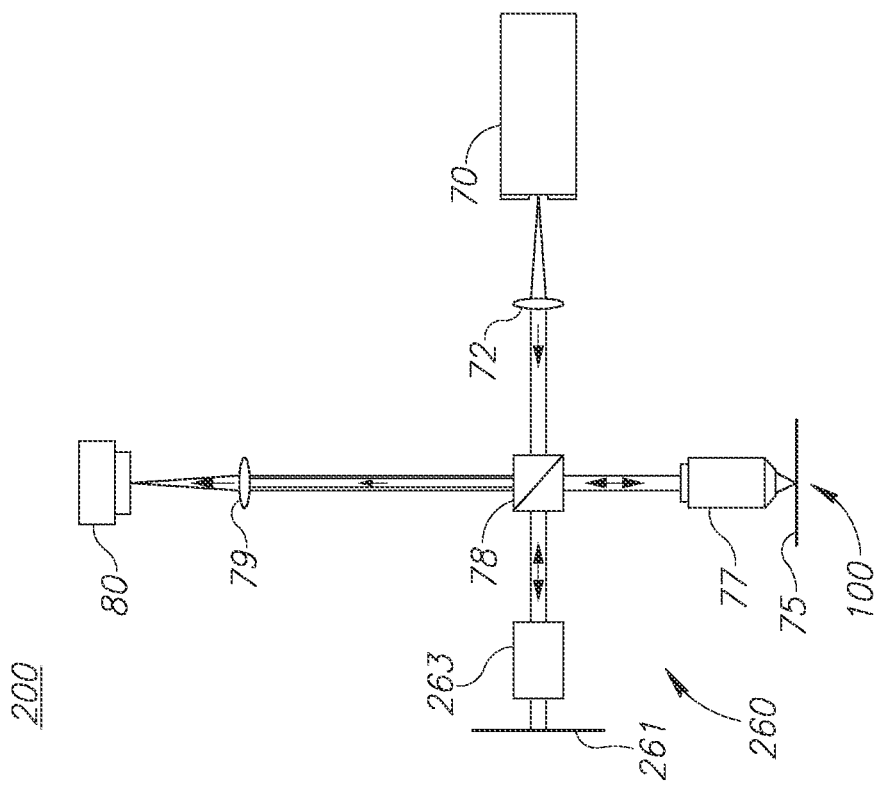
FIG. 6D is a high level schematic illustration of optical illumination and measurement systems, according to some embodiments of the invention.
Figure 6C:
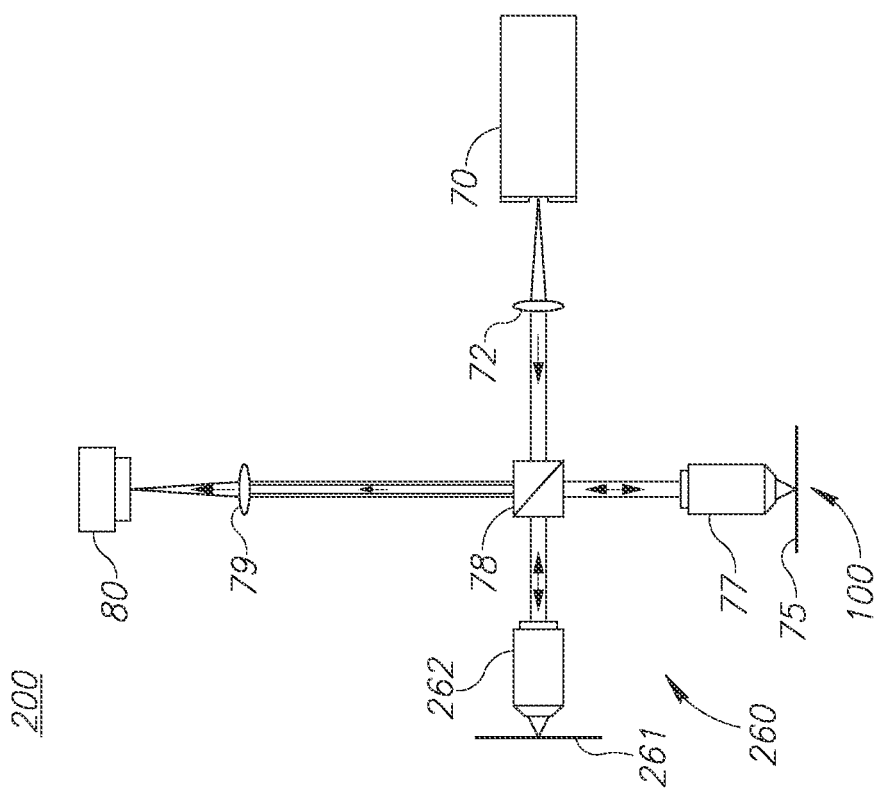
FIG. 6C is a high level schematic illustration of optical illumination and measurement systems, according to some embodiments of the invention.

FIGS. 6C and 6D are high level schematic illustrations of optical systems 200 using an interferometer 260 to control illumination beam polarization and remove zeroth order patterns from the measurements. Illumination is provided from source 70 via lens 72 and through beam splitter 78 to interferometer 260, which may comprise a focusing or non-focusing optical elements (262, 263 in FIGS. 6C, 6D, respectively) and a mirror 261, used to yield destructive interference of the zeroth element component (as mirror 261 lacks a periodic structure and hence reflects only the zeroth order of illumination). The illumination beam may additionally be polarized, e.g., according to FIGS. 6A, 6B or otherwise.

Figure 6E:
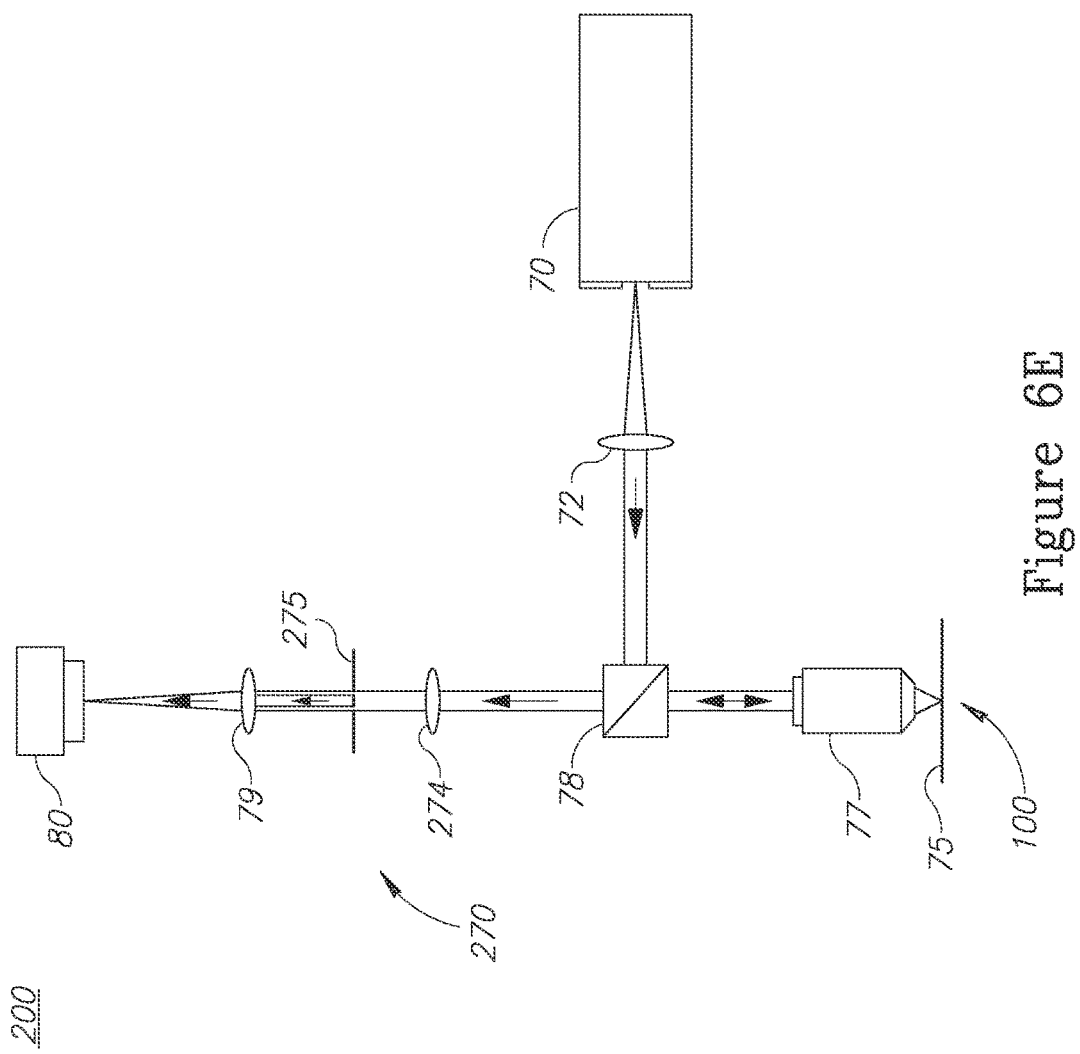
FIG. 6E is a high level schematic illustration of optical illumination and measurement systems, according to some embodiments of the invention.

FIG. 6E schematically illustrates a physical zeroth order blocker 270, designed according to principles taught in U.S. Pat. No. 7,528,941. For this optical configuration target 100 must be periodic; the illumination wavelength and target pitch are chosen to create spatial separation between the reflected orders at pupil plane 275 (after focusing by lens 274). The zeroth order is then blocked geometrically (note that the central section of the measurement beam is blocked after pupil plane 275 the arrow is drawn in the blocked region). The illumination beam may additionally be polarized, e.g., according to FIG. 6A, 6B or otherwise.

Figure 6H:
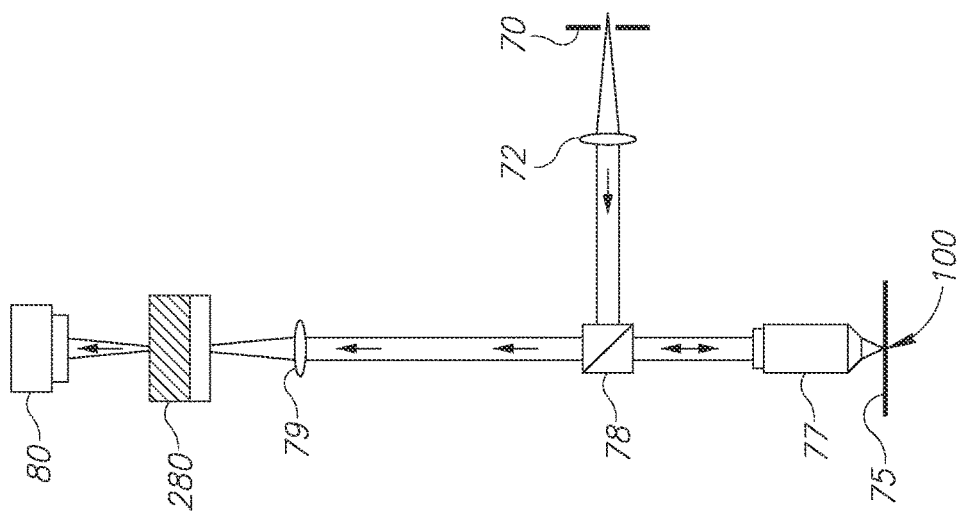
FIG. 6H is a high level schematic illustration of optical illumination and measurement systems, according to some embodiments of the invention.
Figure 6G:
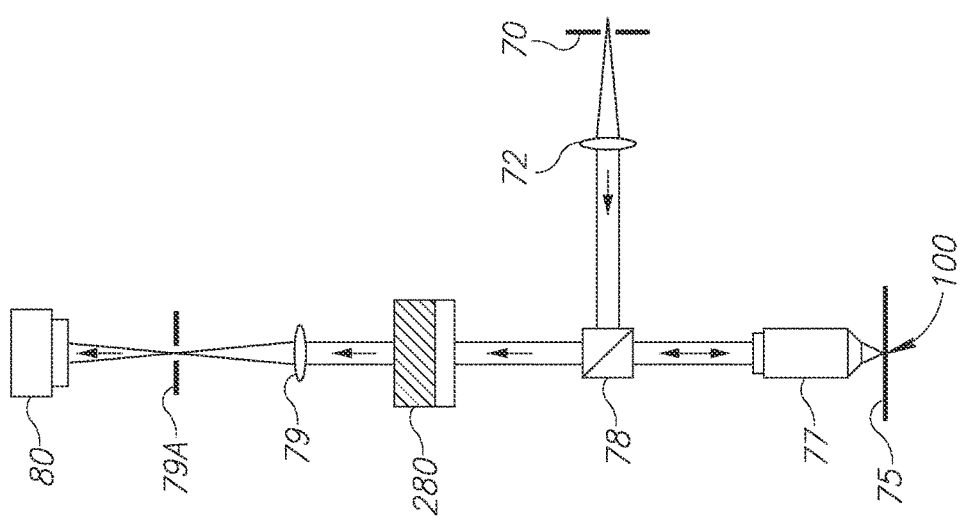
FIG. 6G is a high level schematic illustration of optical illumination and measurement systems, according to some embodiments of the invention.
Figure 6F:
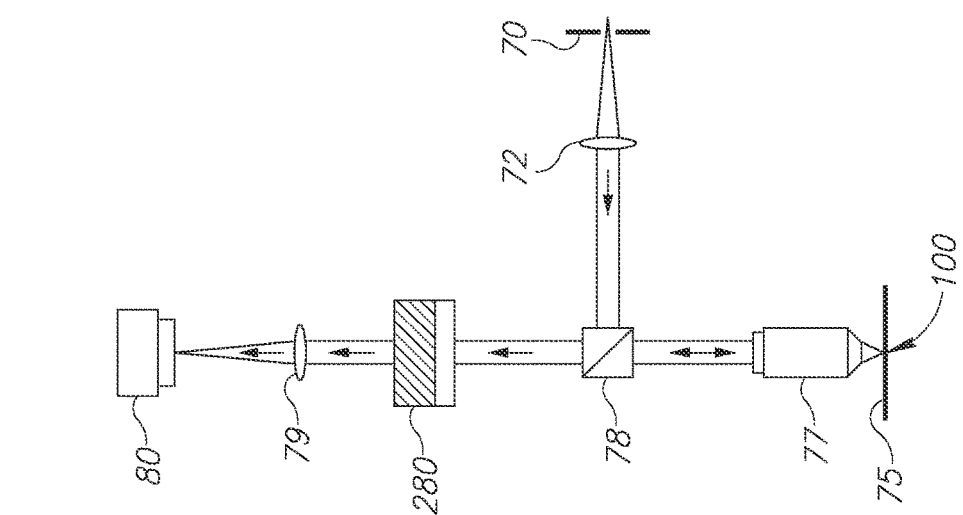
FIG. 6F is a high level schematic illustration of optical illumination and measurement systems, according to some embodiments of the invention.
Figure 6J:
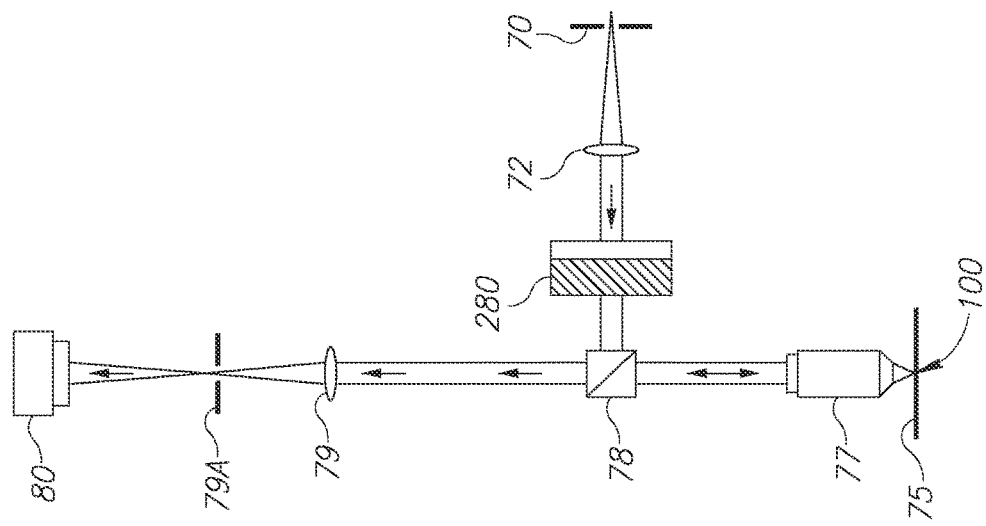
FIG. 6J is a h level schematic illustration of optical illuminati and measurement systems, according to some embodiments of the invention.
Figure 6I:
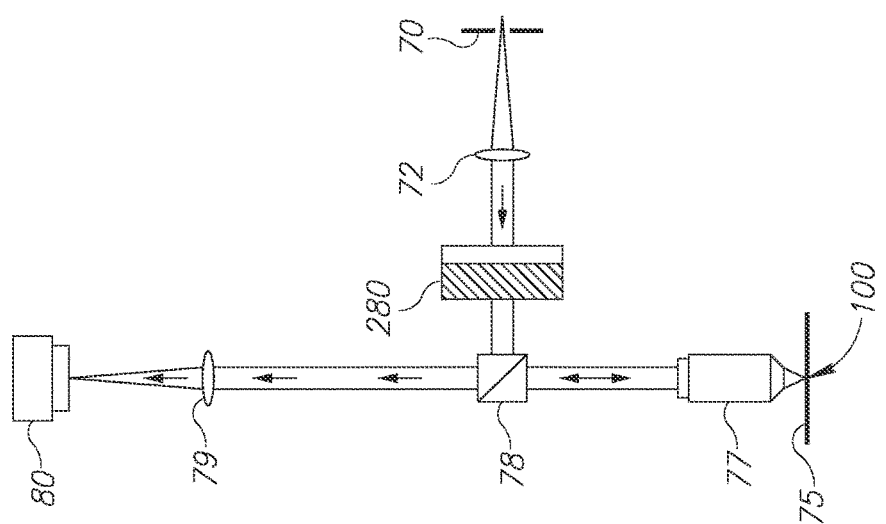
FIG. 6I is a high level schematic illustration of optical illumination and measurement systems, according to some embodiments of the invention.

FIGS. 6F-6J are high level schematic illustrations of optical systems having a variable retarder polarizer 280, for measuring targets 100 using polarized light, according to some embodiments of the invention. FIGS. 6F-6H schematically illustrate embodiments in which the reflected (collection) beam is polarized by variable retarder polarizer 280, while FIGS. 6I-6J schematically illustrate embodiments in which the incident, beam is polarized by variable retarder polarizer 280. Notation of the components and the optical elements (source 70, lens 72, beam splitter 78, objective 77, wafer 75, lens 79 and detector 80) is similar to the notation in FIGS. 6A-6E, the numeral 79A denotes an aperture at the pupil plane. FIG. 6F illustrates an optical system which may be used for imaging measurements, while FIGS. 6G-6H illustrates optical systems which may be used for scatterometry measurements. FIGS. 6I and 6J illustrate optical systems which may be used for imaging and scatterometry measurements, respectively.

Figure 6M:
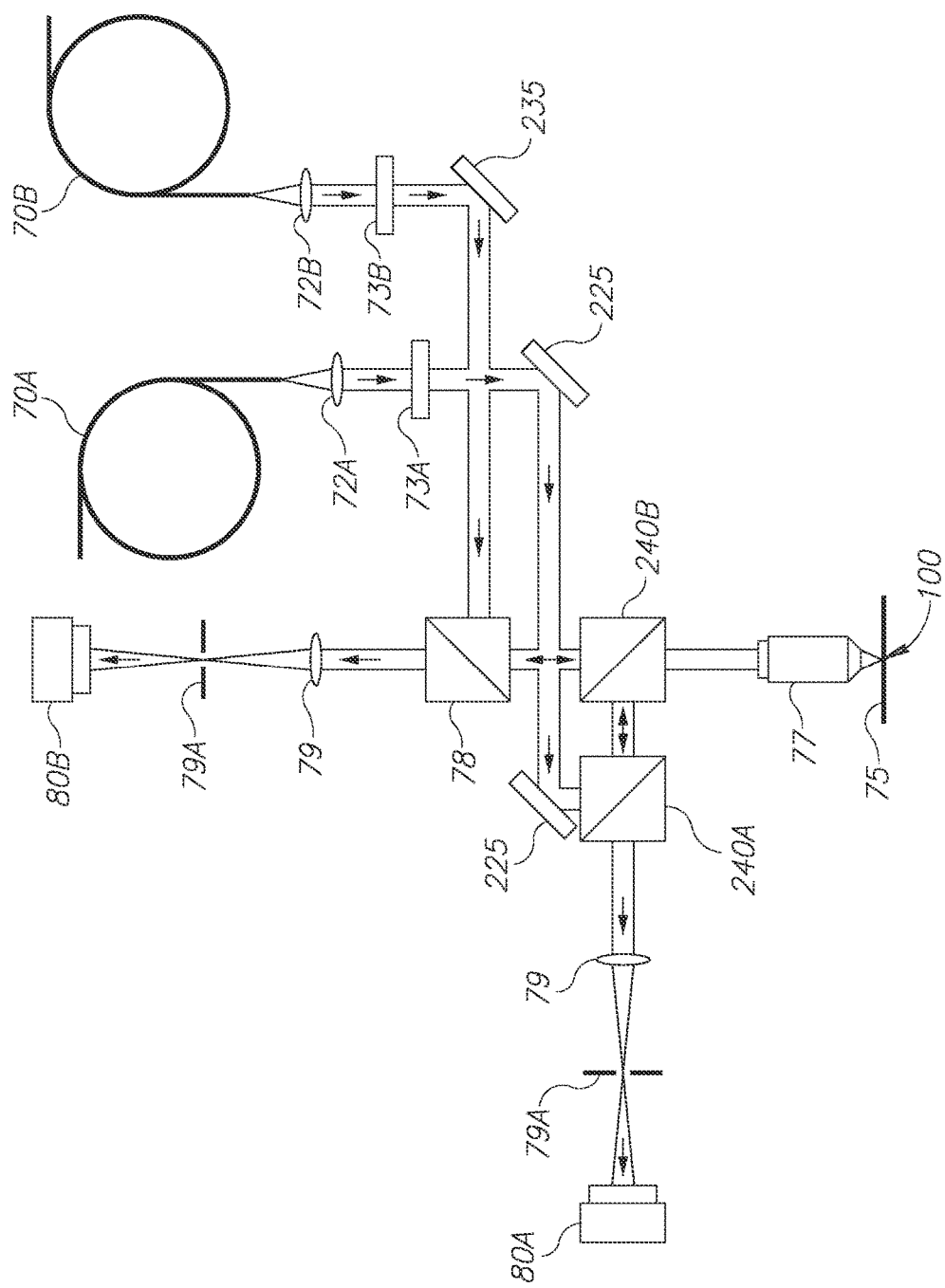
FIG. 6M is a high level schematic illustration of optical illumination and measurement systems, according to some embodiments of the invention; and, FIG. 7 is a high level flowchart illustrating a method, according to some embodiments of the invention.

FIGS. 6K-6M are high level schematic illustrations of optical systems having a variable retarder polarizer 280, for measuring targets 100 using polarized light, according to some embodiments of the invention. FIGS. 6K and 6L schematically illustrate sources for polarized illumination, resulting in two types of polarized light, e.g., s-polarized and p-polarized 70A, 70B respectively. FIG. 6K illustrates use of Polarizing Beam Splitter (PBS) 210 with shutters 220, 230 (as in FIG. 6A) and FIG. 6L illustrates use of variable retarder polarizer 280 instead of shutters 220, 230, in both cases differently polarized light is delivered via respective couplers and fibers 70A, 70B to the measurement part schematically illustrated in FIG. 6M. FIG. 6M schematically illustrates the measuring part, in which the s- and p-polarized beams from respective sources 70A, 70B are delivered via respective lenses 72A, 72B, s- and p-apodizers 73A, 73B, respective mirrors 225, 235 to PBS 240A, 240B which introduce the polarized beams into beam splitter 78 and upon target 100 and deliver the reflected beams to respective s- and p-detectors 80A, 80B.

Advantageously, disclosed optical metrology targets in which the contrast comes from different polarization properties rather than or in addition to difference in the filling factor of different materials may be designed to be fully process compatible and designed according to the device parameters (e.g., with respect to critical dimension and pitch). Polarization of the illumination and/or the collection beam in different configurations may be used to enhance the contrast of the disclosed targets. The targets and measurement with polarized light may furthermore facilitate estimation of the line ends' uniformity and the line edge roughness of device-like features using optical overlay metrology. Moreover, each group of orientation line spaces or combination of different orientation lines may be used as targets for OCD applications, e.g., for monitor and control of scanner focus and dose.

Figure 7:
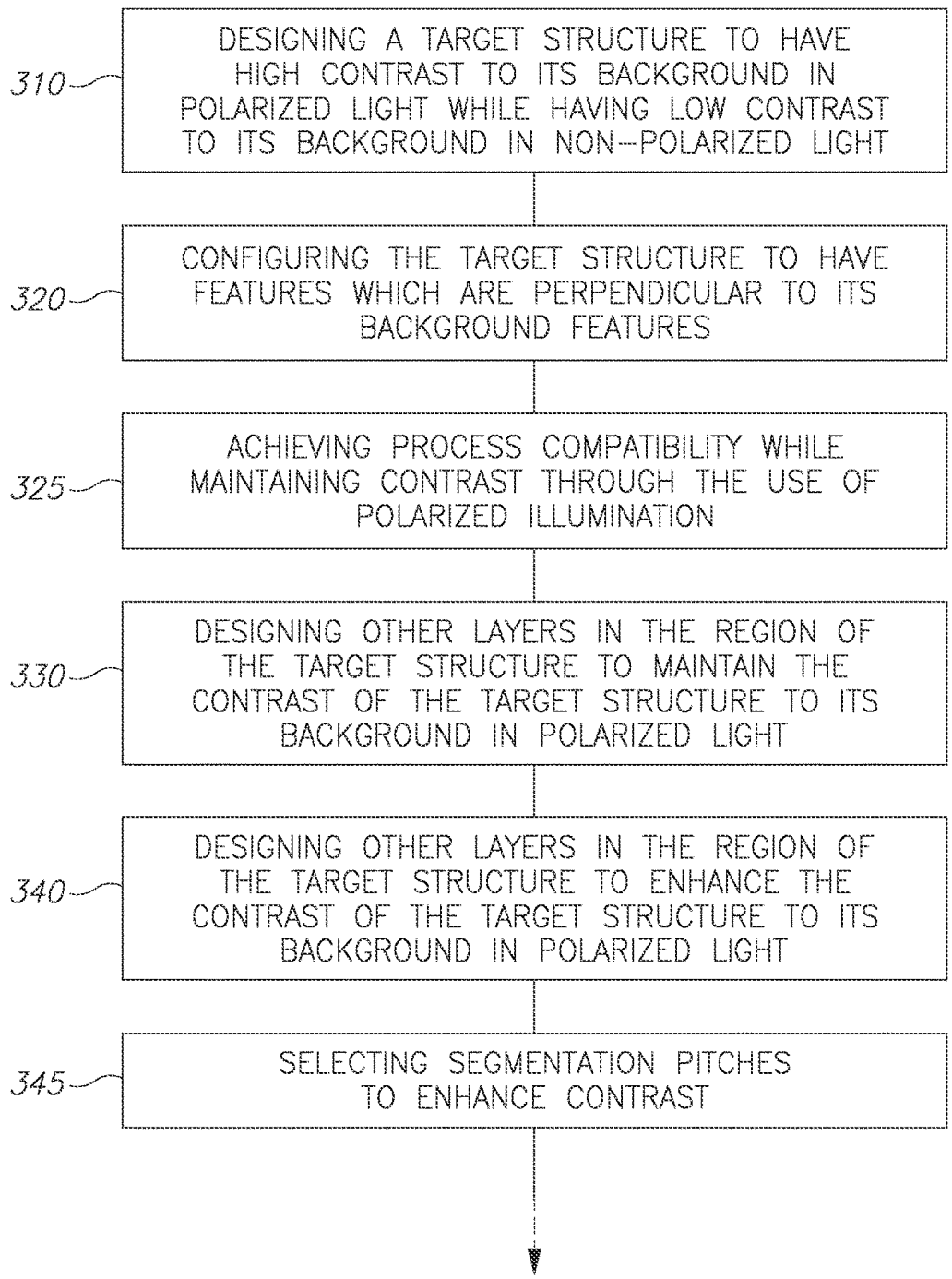

FIG. 7 is a high level flowchart illustrating a method 300, according to some embodiments of the invention. Method 300 may comprise stages for designing, producing and/or measuring targets 100, such as any of the following stages, irrespective of their order. Stages of method 300 may be at least partly carried out by at least one computer processor (stage 370). Certain embodiments comprise computer program products comprising a computer readable storage medium having computer readable program embodied therewith. The computer readable program may be configured to carry out, at least partially, any of the stages of method 300. The disclosed invention comprises target design files and targets designed and produced according to stages of method 300, as well as metrology measurements of any of the disclosed metrology targets.

Method 300 comprises designing a target structure to have a high contrast above a specific contrast threshold to its background in polarized light while having a low contrast below the specific contrast threshold to its background in non-polarized light (stage 310). Method 300 may further comprise configuring the target structure to have features which are perpendicular to background features of the target structure (stage 320). Method 300 comprises designing the target structure to be fully process-compatible with respect to a production process thereof and thus achieve process compatibility while maintaining contrast through the use of polarized illumination (stage 325).

In certain embodiments, method 300 may further comprise designing additional layers in a region of the target structure to maintain (stage 330) or to enhance (stage 340) the contrast of the target structure to its background in polarized light. In certain embodiments, method 300 further comprises selecting segmentation pitches to enhance contrast (stage 345). Method 300 may further comprise spacing the target structure from background features thereof to a specified extent (stage 350). In certain embodiments, method 300 further comprises using two or more measurements, possibly with different illumination characteristics (such as polarization, wavelengths, focus etc.) to enhance the contrast and to derive additional information from comparison of the measurements (stage 355). Respective metrology measurements of target 100 and/or according to method 300 are likewise part of the present disclosure. Method 300 may comprise measuring the target structure repeatedly under varying illumination conditions and deriving additional measurement data from the multiple measurements, and the metrology measurements may comprise respective multiple measurements under varying illumination conditions and the derived additional measurement data.

Method 300 may further comprise producing the designed target structure (stage 375) and respective target design files. Such design files are part of the present disclosure as well. Method 300 may further comprise adapting any target type to be process compatible and exhibit contrast under polarized illumination (stage 365).

In certain embodiments, method 300 may further comprise measuring the target structure in polarized light to distinguish it from its background (stage 380) and possibly adjusting measurement conditions for each layer to enhance the contrast between the target structure contrast and its background (stage 360). Measuring 380 may be carried out using any of: coupled polarizers, alternating polarizers in an optical path of the measurement, an interferometer, variable retarder polarizers (applied to the illumination and/or collection beams, a zero order blocker at a pupil plane and/or polarized light sources or combinations thereof (stage 390).

Advantageously, the disclosed invention provides optical metrology targets 100 in which the contrast comes from different polarization properties rather than (or in addition to) difference in the filling factor of different materials. Respective methods 300 provide guidelines to design principles of such targets. The optical metrology targets may be designed to be fully process compatible by being fully designed according to the device parameters with respect to critical dimension and pitch). The disclosed invention further provides optical system capable of measuring such targets using polarization and/or zero order blocking and/or zero order destructive interference. Polarization of the illumination and/or the collection beam may be implemented in different configurations to enhance the contrast of target structures 120 with respect to their backgrounds 110.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method of measuring a metrology target element comprising:
illuminating, with illumination of a selected polarization, the metrology target element including a segmented target structure having a first segmentation direction, a segmented background region having a second segmentation direction perpendicular to the first segmentation direction, wherein the segmented target structure and the segmented background region are formed in a single layer, wherein an area of the segmented target structure and an area of the segmented background region combine to substantially fill an area of the metrology target element, wherein at least one of a segmentation pitch of the segmented background region or a segmentation pitch of the segmented target structure provide a first contrast above a specified contrast threshold under polarized light and a second contrast below the specific contrast threshold to the segmented background region in non-polarized light,
measuring illumination reflected from the metrology target element, wherein the illumination measured is at least one of polarized light above the specific contrast threshold to the segmented background region or non-polarized light below the specific contrast threshold to the segmented background region;

measuring one or more side wall angles of the segmented target structure; and determining one or more distances between the segmented target structure and the segmented background region along a boundary between the segmented target structure and the segmented background region based on the measured one or more side wall angles of the segmented target structure.

2. The method of claim 1, wherein one or more segmentation features of the segmented target structure and one or more segmentation features of the segmented background region provide a selected contrast level between the segmented target structure and the segmented background region when illuminated with light of a selected polarization.

3. The method of claim 2, wherein a difference between the one or more segmentation features of the segmented target structure and the one or more segmentation features of the segmented background region provide the selected contrast level between the segmented target structure and the segmented background region when illuminated with light of a selected polarization.

4. The method of claim 3, wherein at least one of the one or more segmentation features of the segmented target structure or the one or more segmentation features of the segmented background region comprise:

at least one of segmentation pitch, critical dimension of segments, segmentation direction or segmentation pattern.

5. The method of claim 2, wherein the segmented background region is formed within the segmented target structure at one or more additional layers such that the segmented background region overlaps the segmented target structure.

6. The method of claim 2, wherein the segmented background region is spaced from the segmented target structure by a selected distance.

7. The method of claim 2, wherein the illuminating the metrology target element with illumination of a selected polarization comprises:

illuminating the metrology target element with illumination of at least one of linear polarization, circular polarization, s-polarization or p-polarization.

8. The method of claim 2, wherein the illuminating the metrology target element with illumination of a selected polarization comprises:

illuminating the metrology target element with illumination having modulated polarization.

9. The method of claim 2, the measuring illumination reflected from the metrology target element comprises:

measuring one or more first order diffraction patterns from the reflected illumination following removing of one or more zeroth order diffraction patterns from the reflected illumination.

10. The method of claim 1, further comprising:

identifying a difference between a first measured side wall angle and a second measured side wall angle; and determining at least one of a pattern placement error or edge quality metric based on the identified difference between the first measured side wall angle and the second measured side wall angle.

11. An apparatus for measuring a metrology target element comprising:

a light source for generating illumination;

a set of optical elements configured to modify the illumination from the light source to form illumination of a selected polarization, wherein the set of optical elements are configured to direct the illumination of the selected polarization to a metrology target element, wherein the set of optical elements are configured to collect illumination reflected from the metrology target element, wherein the metrology target element includes a segmented target structure having a first segmentation direction and a first pitch and a segmented background region having a second segmentation direction and a second pitch perpendicular to the first segmentation direction, wherein the segmented target structure and the segmented background region are formed in a single layer, wherein an area of the segmented target structure and an area of the segmented background region combine to substantially fill an area of the metrology target element, wherein the segmented background region and the segmented target structure are formed such that at least one of the first pitch or the second pitch provides the segmented target structure a first contrast above a specific contrast threshold to the segmented background region in polarized light and a second contrast below the specific contrast threshold to the segmented background region in non-polarized light;

a detector for measuring the illumination reflected from the metrology target element; and at least one computer processor configured to:

measure one or more side wall angles of the segmented target structure; and determine one or more distances between the segmented target structure and the segmented background region along a boundary between the segmented target structure and the segmented background region based on the measured one or more side wall angles of the segmented target structure.

12. The apparatus of claim 11, wherein one or more segmentation features of the segmented target structure and one or more segmentation features of the segmented background region provide a selected contrast level between the segmented target structure and the segmented background region when illuminated with light of a selected polarization.

13. The apparatus of claim 12, wherein a difference between the one or more segmentation features of the segmented target structure and the one or more segmentation features of the segmented background region provide the selected contrast level between the segmented target structure and the segmented background region when illuminated with light of a selected polarization.

14. The apparatus of claim 13, wherein at least one of the one or more segmentation features of the segmented target structure or the one or more segmentation features of the segmented background region comprise:

at least one of segmentation pitch, critical dimension of segments, segmentation direction or segmentation pattern.

15. The apparatus of claim 11, wherein the segmented background region is formed within the segmented target structure at one or more additional layers such that the segmented background region overlaps the segmented target structure.

16. The apparatus of claim 11, wherein the segmented background region is spaced from the segmented target structure by a selected distance.

17. The apparatus of claim 11, wherein the selected polarization comprises:

at least one of linear polarization, circular polarization, s-polarization or p-polarization.

18. The apparatus of claim 11, wherein the selected polarization comprises:
modulated polarization.

19. The apparatus of claim 11, wherein the detector is further configured to measure one or more first order diffraction patterns from the reflected illumination following removing of one or more zeroth order diffraction patterns from the reflected illumination.

20. The apparatus of claim 11, wherein the at least one computer processor is further configured to:
identify a difference between a first measured side wall angle and a second measured side wall angle; and
determine at least one of a pattern placement error or edge quality metric based on the identified difference between the first measured side wall angle and the second measured side wall angle.

* * * * *